United States Patent
Haessler

(10) Patent No.: US 8,914,111 B2
(45) Date of Patent: Dec. 16, 2014

(54) DEVICES AND METHODS FOR STIMULATING NERVES

(71) Applicant: FemPulse, LLC, Incline Village, NV (US)

(72) Inventor: Alexandra Haessler, Larkspur, CA (US)

(73) Assignee: FemPulse, LLC, Incline Village, NV (US)

( * ) Notice: Subject to any disclaimer, the term of this patent is extended or adjusted under 35 U.S.C. 154(b) by 0 days.

(21) Appl. No.: 13/844,472

(22) Filed: Mar. 15, 2013

(65) Prior Publication Data

US 2014/0058474 A1    Feb. 27, 2014

Related U.S. Application Data

(63) Continuation-in-part of application No. 13/492,855, filed on Jun. 9, 2012, now Pat. No. 8,788,040.

(51) Int. Cl.
| | | |
|---|---|---|
| *A61B 5/0492* | (2006.01) | |
| *A61B 5/04* | (2006.01) | |
| *A61N 1/05* | (2006.01) | |
| *A61N 1/36* | (2006.01) | |
| *A61B 5/00* | (2006.01) | |
| *A61B 5/0488* | (2006.01) | |

(52) U.S. Cl.
CPC .......... *A61N 1/36007* (2013.01); *A61N 1/0514* (2013.01); *A61B 5/0492* (2013.01); *A61B 5/411* (2013.01); *A61N 1/05* (2013.01); *A61B 5/04882* (2013.01)
USPC ................................ 607/39; 600/138; 607/2

(58) Field of Classification Search
None
See application file for complete search history.

(56) References Cited

U.S. PATENT DOCUMENTS

| | | | |
|---|---|---|---|
| 4,515,167 A | 5/1985 | Hochman | |
| 4,607,639 A | 8/1986 | Tanagho et al. | |
| 4,771,779 A | 9/1988 | Tanagho et al. | |
| 4,881,526 A | 11/1989 | Johnson et al. | |
| 4,909,263 A | 3/1990 | Norris | |
| 5,370,671 A | 12/1994 | Maurer et al. | |
| 5,662,699 A | 9/1997 | Hamedi et al. | |
| 5,702,428 A | 12/1997 | Tippey et al. | |
| 6,055,456 A | 4/2000 | Gerber | |
| 6,086,549 A | 7/2000 | Neese et al. | |
| 6,185,465 B1 | 2/2001 | Mo et al. | |
| 6,356,777 B1 * | 3/2002 | Garfield et al. | ............... 600/372 |
| 6,402,683 B1 | 6/2002 | Marty | |
| 6,418,930 B1 | 7/2002 | Fowler | |
| 6,428,467 B1 | 8/2002 | Benderev | |
| 6,432,037 B1 | 8/2002 | Eini et al. | |
| 6,625,495 B1 | 9/2003 | Alon et al. | |
| 6,741,895 B1 | 5/2004 | Gafni et al. | |
| 6,964,643 B2 | 11/2005 | Hovland et al. | |
| 7,079,882 B1 | 7/2006 | Schmidt | |
| 7,369,894 B2 | 5/2008 | Gerber | |
| RE41,463 E | 7/2010 | Boutos | |
| 7,957,794 B2 | 6/2011 | Hochman | |
| 7,963,977 B2 | 6/2011 | Brockman | |
| 2004/0030360 A1 | 2/2004 | Eini et al. | |
| 2005/0113877 A1 * | 5/2005 | Spinelli et al. | .................. 607/39 |
| 2009/0036945 A1 | 2/2009 | Chancellor et al. | |

(Continued)

*Primary Examiner* — Carl H Layno
*Assistant Examiner* — Jon Eric C Morales
(74) *Attorney, Agent, or Firm* — Jens E. Hoekendijk

(57) ABSTRACT

A device for stimulating nerves adjacent the vagina includes a nerve stimulating element coupled to a body. The nerve stimulating element is positioned to stimulate the vesical, Frankenhauser's and/or inferior hypogastric plexuses. The device may reside in the vaginal fornices.

6 Claims, 20 Drawing Sheets

(56) References Cited

U.S. PATENT DOCUMENTS

| | | |
|---|---|---|
| 2009/0076565 A1 | 3/2009 | Surwit |
| 2009/0222058 A1 | 9/2009 | Craggs |
| 2009/0228067 A1 | 9/2009 | Boyd et al. |
| 2009/0270963 A1 | 10/2009 | Pelger et al. |
| 2012/0215280 A1 | 8/2012 | Peddicord |

* cited by examiner

A-A
battery

B-B
control

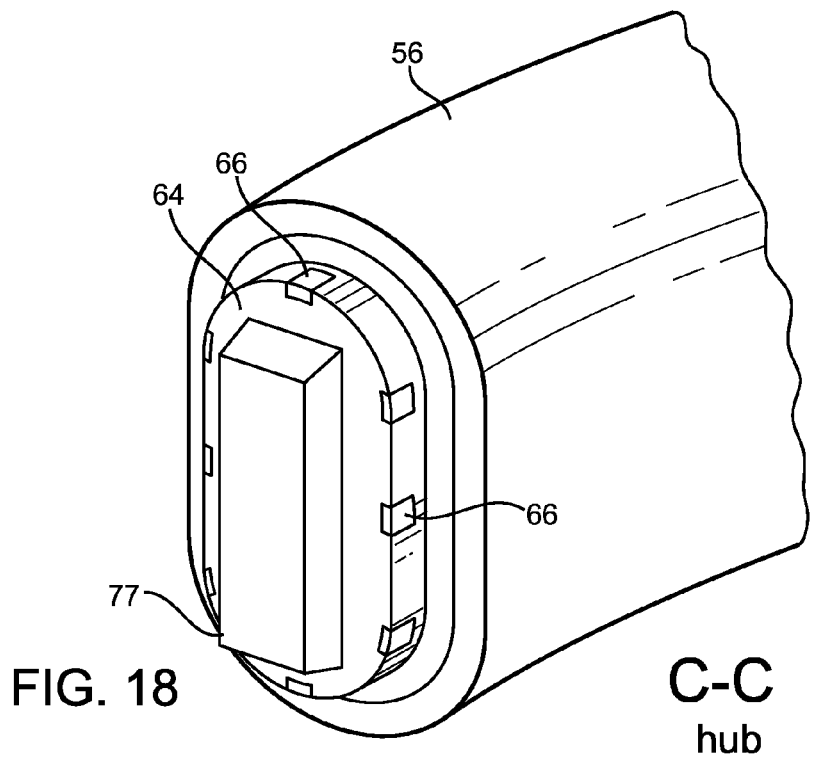
FIG. 18          C-C
                 hub
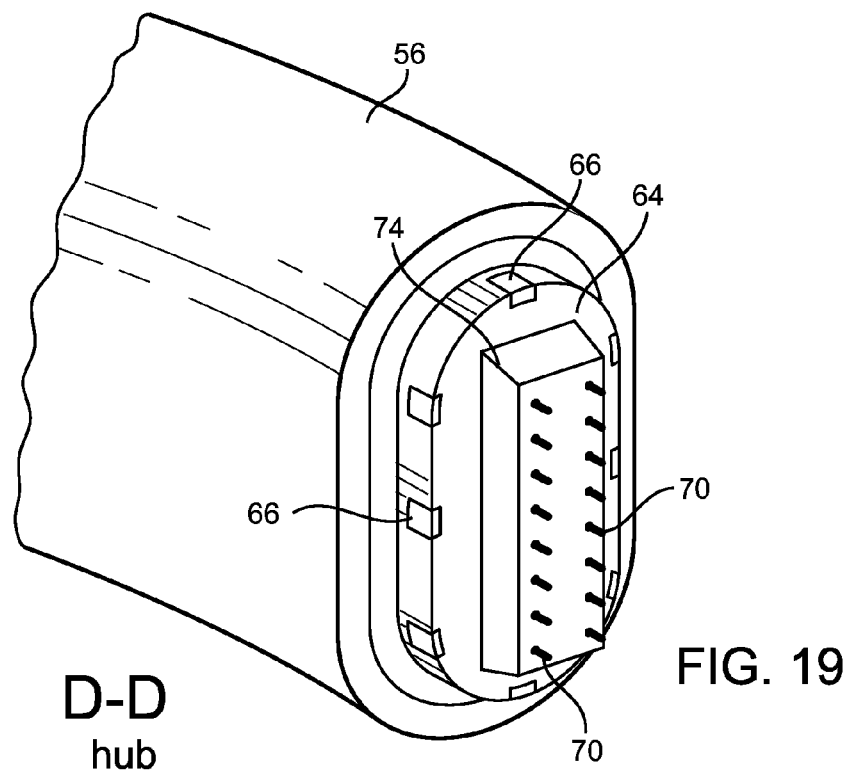
D-D              FIG. 19
hub

DEVICES AND METHODS FOR STIMULATING NERVES

CROSS-REFERENCE TO RELATED APPLICATIONS

The present application is a continuation in part of U.S. application Ser. No. 13/492,855, filed Jun. 9, 2012, by Alexandra Haessler, which is hereby incorporated by reference.

BACKGROUND

Millions of women suffer from increased urinary urgency, frequency, incontinence, incomplete bladder emptying and irritative bladder conditions. There are two main types of incontinence, urge incontinence and stress incontinence, which have different physiological causes and different treatment options. Many women suffer from mixed incontinence, having both conditions.

Stress incontinence is largely the result of weakened ligaments, pelvic floor tissue and vaginal support, ultimately allowing the urethra to drop open in the setting of increased intraabdominal pressure. The process leading to stress incontinence is primarily mechanical and is associated with supportive tissue under the distal anterior vaginal wall. Strengthening the pelvic floor and supporting the urethra and/or bladder neck are safe and effective treatments for stress incontinence.

Urinary urgency, frequency, urge incontinence, incomplete bladder emptying, and nocturia represent a more complex process that is greatly neurologically mediated. Urinary urgency is marked by a strong and often uncomfortable urge to void that is difficult to suppress. Urge incontinence is defined by involuntary leakage of urine in the setting of urgency. The conditions noted above and other irritative bladder conditions may result from abnormal sensitivity of autonomic bladder nerves that prematurely communicate "fullness" to the central nervous system. These conditions may also result from erroneous nerve function in the central nervous system that allows the bladder to empty at inappropriate times. The underlying cause of these problems may be multifactorial. Ultimately, it is the autonomic nervous system that communicates bladder sensation, discomfort, or "fullness" and coordinates bladder filling and emptying.

Incomplete bladder emptying or urinary retention may result from inappropriate autonomic nerve signaling to the urethra and/or bladder. Some medical treatments are aimed at altering autonomic signal to the urethra, such that urethral tone is lessened. Others work by increasing bladder muscle tone by activating autonomic receptors in the bladder to cause a bladder contraction.

Many treatments of irritative bladder conditions are aimed at modifying nerve signaling between the bladder and the central nervous system. The goal is to affect both the afferent signals to the central nervous system that signal irritation, urgency, pressure or a sense of fullness and/or the efferent nerve signal that can trigger a rise in bladder pressure, cause discomfort, or leakage. Autonomic nerves transmit these signals. Treatment for urinary urgency, frequency, nocturia and urge incontinence is multifaceted, attempting to affect nerve signaling with behavioral, dietary, medical and physical therapies.

Urinary urge incontinence medications attempt to inhibit bladder contractions by disrupting signals between the autonomic nerves and the urinary tract. These drugs are not adequately effective for the majority of patients and also have significant systemic side effects that limit usage. Discontinuation rates at 6 months are well over 50% due to the high cost, lack of adequate effectiveness, and side effects. There are also contraindications to use, most of which are conditions affecting the elderly population that desires treatment for lower urinary tract symptoms.

An aggressive pelvic floor physical therapy regimen incorporating education, lifestyle, and dietary changes along with pelvic floor exercise training can be a reasonably effective treatment for urgency, frequency and urge incontinence in some patients. It is not clear how well exercise alone works to control urge related symptoms, as a large portion of the benefit gained from physical therapy is the result of education, cognitive-behavioral techniques, diet and lifestyle change. Patients are not often compliant beyond the short term, as the regimen can be costly, time consuming and difficult to comply with over time.

The goal of most pelvic floor exercises is to strengthen the muscles of the pelvic floor and increase nerve "tone." These exercises activate the somatic nerves in order to cause pelvic floor muscle contraction. This is primarily a treatment for stress incontinence. A pelvic floor muscle contraction can secondarily affect autonomic nerves to the bladder via a spinal cord reflex arc. These exercises may dampen the signal to urinate or prevent leakage. They do not necessarily prevent the more common overactive bladder symptoms that occur before one has time to perform a contraction, such as a spontaneous sense of urgency or waking at night to void. It has been shown that urinary urgency alone, without leakage, is more bothersome to patients than urinary leakage alone. Effective treatment needs to prevent the spinal cord from perceiving inappropriate sensations in the first place.

Neuromodulation of autonomic nerves has become a useful treatment method for lower urinary tract symptoms, such as urgency, frequency, incontinence, incomplete bladder emptying, irritative symptoms, incomplete bladder emptying, fecal incontinence and related conditions. One technique involves an implanted stimulation lead over the S3 nerve root. It can be a successful treatment for patients who have failed other treatments.

Although use of the surgical implant over the S3 nerve root has been successful, the treatment has drawbacks. The main disadvantage is that the device requires surgical implantation of small electrical leads through a foramen in the sacrum and a stimulator device within the soft tissue above the gluteus maximus. Implantation typically requires two surgical procedures, exposure to radiation, and often requires additional surgery to revise or remove the components. It has also been reported that over 25% of patients will require surgical revision of either the implanted battery or lead to manage complications. Additionally, the current surgical implant often needs to be removed for some types of MRI. The device is also extremely expensive. In general, patients prefer less effective alternative therapies, as they often do not think bladder symptoms warrant surgery or they are not comfortable with the idea of a surgical implant.

Another drawback of the conventional surgical implant is that the stimulation occurs at the level of the nerve root, so somatic fibers traveling in the S3 nerve root are also stimulated before they branch off into somatic nerves. These nerves can cause the patients to feel vulvar, vaginal, anal and lower extremity muscle contractions or tingling. Still another limitation of the implantable stimulator is that the same one, or occasionally two, nerve roots are available and subject to all of the stimulation. As a result, the nerve becomes less responsive due to habituation rendering the lead less effective or ineffective. This phenomenon has been well established. Due to these many drawbacks, including risk of surgery, complications associated with the implant, cost, reduced effectiveness over time, and somatic symptoms associated with the implanted S3 sacral nerve modulator, this treatment has not been widely adopted despite its effectiveness.

The existing non-surgical electrical stimulation therapies include devices that are positioned in the vagina thereby avoiding some drawbacks of the surgical implant. However, these devices are often less effective and have their own drawbacks. Many conventional devices positioned in the vagina direct electrical impulses in the lower or distal vagina and/or adjacent to the pelvic floor. Electrical signals are sent through the vagina to paravaginal tissue, targeting nerves adjacent the pelvic floor muscles or the muscles themselves. The goal suggested by these conventional methods is generally to stimulate nerves adjacent the pelvic floor and to increase pelvic floor tension. Many of these therapies attempt to treat stress incontinence and/or simulate pelvic floor exercises. Yet bladder filling, emptying and sensation are mediated by autonomic nerves, not somatic nerves. The inventor believes that these devices and therapies are often not as effective at treating urinary urgency, incontinence, nocturia, incomplete bladder emptying or other lower urinary tract symptoms as an implanted sacral nerve modulator because they do not sufficiently isolate stimulation to autonomic nerves.

A major limitation of these vaginal stimulation devices for treating most irritative urinary tract symptoms is that they indiscriminately send electrical impulses to both somatic and some distal autonomic nerve fibers adjacent to the lower and mid-vagina. They also often target somatic nerves, such as the pudendal nerve and its distal branches. The somatic nerves do not directly control bladder filling, emptying, or sensation. Activation of somatic nerves can cause increased pelvic floor tension, discomfort, and pain associated with pudendal nerve activation. Such conditions may actually contribute to urinary urgency, frequency and voiding dysfunction. Somatic nerves are quite sensitive, so the electrical impulses can be perceived even at low intensity, thereby limiting the full range of treatment protocols or precluding therapy altogether.

Thus, the inventor believes that the problem with present neuromodulation treatment methods is that they either require surgical implantation or, for vaginally inserted devices, the stimulation does not adequately target important autonomic nerve structures yet influences muscles and somatic nerves in the lower vagina providing less effective therapy for autonomically mediated urinary tract symptoms and contributing to undesirable side effects. Thus, optimal therapy would stimulate the autonomic nerves that mediate signal between the urinary tract and the central nervous system while avoiding activation of the pelvic floor and associated somatic nerves. Optimally, neuromodulation would be delivered directly to the autonomic nerves at the "gateway" between the urinary tract and the spinal cord while avoiding pelvic floor muscle and nerve activation.

SUMMARY

The present invention provides devices and methods for targeting autonomic nerves while minimizing transmission of stimulus to pelvic floor muscles and non-target nerves, specifically, somatic nerves adjacent to the lower or mid-vagina. The present invention is positioned to stimulate autonomic plexuses and autonomic nerves at the "gateway" between the lower urinary tract and the spinal cord while avoiding pelvic floor muscle and nerve activation. In specific embodiments and methods, the present invention targets the inferior hypogastric plexus (or pelvic plexus), left and right Frankenhauser's plexus (or Lee's plexus) and the vesical plexus. These plexuses may, of course, be called by other names such as Lee's plexus as another name for Frankenhauser's plexus without departing from the invention. Furthermore, the Frankenhauser's plexus refers to both left and right Frankenhauser's plexuses collectively. Unless otherwise specified, use of Frankenhauser's plexus or plexuses shall mean both plexuses.

In one aspect of the present invention, a device for stimulating nerves is positioned in the upper half of the vagina, and in specific embodiments in the vaginal fornices, so that the stimulus intended for the target nerves does not adversely influence non-target somatic nerves, such as the pudendal nerve or its branches, adjacent to the distal or lower half of the vagina. Reducing side effects and possible urinary tract symptoms due to stimulating somatic nerves are thereby avoided in accordance with the present invention.

The present invention treats urologic, gynecologic, colorectal and pain conditions in women with neuromodulation of nerves via electrical stimulation (and other modalities) delivered by a unique, self-retained, indwelling vaginal device that resides in the fornices of the vagina (or uppermost portion of the vagina in women without a cervix) and targets specific autonomic plexuses which communicate with associated nerves traveling to and from genitourinary and pelvic structures. The neuromodulation of the present invention stimulates the nerve plexuses to change a signal transmitted by the nerve plexuses to the associated autonomic nerves.

Referring to FIG. 1, autonomic nerve signals traveling to and from the bladder, urethra, rectum, vagina, uterus, peritoneum and other pelvic structures travel through the inferior hypogastric plexus IHP, carrying the signal between pelvic structures and the spinal cord. The inferior hypogastric plexus IHP is the gateway between the visceral (bladder, gynecologic, rectum) organs and the central nervous system. The IHP is a coalescence of both sympathetic and parasympathetic autonomic fibers. The sympathetic fibers run between the thoracic nerve roots (T10-L2) and into the superior hypogastric plexus, then travel towards the IHP via the left and right hypogastric nerves LHN, RHN along the uterosacral ligaments USL. In some cases a portion of the sympathetic fibers may enter the IHP along the undersurface of the cardinal ligaments. These fibers facilitate bladder storage. The parasympathetic nerves travel from the sacral spinal nerve roots (S2-4) in the sacral or pelvic splanchnic nerves, or nervi erigentes towards the pelvic organs, often in association with the pelvic nerve. They facilitate bladder emptying. Sympathetic and parasympathetic fibers coalesce in the IHP over the posterior and lateral surfaces of the upper cervix, just above the vaginal insertion.

Importantly, the vagina terminates at the level of the pericervical ring around the uppermost portion of the cervix, just below the uterosacral ligament USL insertions. The recesses of the most proximal, or uppermost, aspect of the vagina that surround the cervix are called the vaginal fornices VF. The pelvic floor PF surrounds the lower portion of the vagina near the vaginal opening, making the "floor" of the pelvic cavity. The inferior hypogastric plexus IHP is a web-like plexus adjacent to the posterior and lateral cervix at the level of the uterocervical junction and the uterosacral ligament USL insertions, just proximal to the posterior vaginal fornix. Inferior hypogastric plexus IHP fibers also cover the distal uterosacral ligaments and possibly reside in the lower or under-portion of the cardinal ligament just anterior to the USL. For reference, the IHP is generally referred to as a singular structure in the literature, but anatomic studies suggest significant concentrations of these ganglia may be distributed bilaterally, as described above. For purposes of this description and application the IHP, when used herein, will refer to the IHP and any lateral extensions around the cervix or most proximal aspect of the vagina.

Autonomic nerve fibers travel from the IHP around the cervix to the vesical plexus, which communicates with autonomic fibers to innervate the bladder. Some autonomic fibers travel from the IHP to the posterior-lateral aspect of the cervix to right and left Frankenhauser's plexuses FP (also known as Lee's or the uterovaginal plexuses). Frankenhauser's or Lee's plexuses send some nerves upward to innervate the uterus and some nerves inferiorly to innervate the vagina, cervix, urethra, and clitoris. Both of these plexuses may be important in controlling urinary tract function. Autonomic fibers travel between the IHP and the middle rectal plexus to innervate the distal rectum.

Surgical removal of the cervix can result in injury to the hypogastric nerves, IHP, Frankenhauser's plexuses and/or the vesical plexuses. These structures often heal and function well post-operatively. However, they can sustain permanent injury and exhibit chronically altered function resulting in chronic urinary tract conditions and other forms of pelvic organ dysfunction.

As mentioned above, autonomic nerves and somatic nerves have different functions. Autonomic nerves control visceral, internal organ function and some types of pain. The bladder and urethra are innervated by autonomic nerves. Somatic nerves mediate voluntary muscle activity, body movement, and somatic sensation. The pudendal nerve PN and its distal branches mediate voluntary pelvic floor function and some distal vaginal, urethral, anal and genital sensation. The nerve types also have different distributions. For example, autonomic nerves traveling to and from the pelvic organs enter via a proximal and central approach, just above the top of the posterior vagina in the center of the pelvic cavity. The somatic nerves travel to the pelvic floor from an inferior and lateral approach. A problem with prior art devices placed in the vagina is that they stimulate, usually intentionally, somatic nerves adjacent the pelvic floor such as the pudendal nerve and its branches.

Autonomic nerves are responsible for signaling visceral organ or peritoneal pain, such as that caused by endometriosis, dysmenorrhea, interstitial cystitis, irritable bowel syndrome, adhesions and other conditions. Autonomic nerves also influence how visceral organs respond to somatic pain and can be a source of referred pain in a somatic distribution. Autonomic sensation may be transmitted by autonomic (or visceral) sensory fibers, not necessarily sympathetic or parasympathetic fibers.

In an embodiment, the present invention is an indwelling, removable, programmable, stimulation device that is positioned in the fornices of the vagina, thereby optimally targeting autonomic plexuses of the pelvic organs and the distal aspect of the hypogastric nerves. This device will deliver electrical stimulation (and support other therapies, such as application of a magnetic field, medication, or ultrasound) to the plexuses and associated nerves at the autonomic gateway between the pelvic organs and the central nervous system, mainly at the left and right hypogastric nerves, inferior hypogastric plexus, left and right Frankenhauser's plexuses, the vesical plexus and possibly the middle rectal plexuses. Stimulation of these plexuses and distal hypogastric nerves changes a signal sent by these plexuses and nerves to their associated efferent and afferent nerve fibers.

At this location the neuromodulation signal will have more effect than if it were distributed distal to the plexuses, such as with current devices that stimulate and reside lower in the vagina. With more distally stimulating devices some aberrant nerve signal arising above the stimulation site can travel, for example, between the urinary tract and the plexuses or hypogastric nerve above the stimulation site. The same limitations can hinder the effects of the current devices in treating gynecologic, colorectal and pain conditions as well. The device of the present invention, on the other hand, is positioned in the vaginal fornices or upper-most portion of the vagina thereby optimizing stimulation to the autonomic nerves and plexuses that control the sensation and function of the pelvic organs, including the bladder.

In a preferred embodiment, a ring-like device with an electrode, or a plurality of electrodes, will reside in the fornices, adjacent to the plexuses that surround the cervix. The device will also be able to target the junction between the left and right hypogastric nerves (that travel to and from the IHP along the uterosacral ligaments) and the IHP. An advantage of the present invention is that positioning the device in the fornices allows access to the collection of plexuses (vesical, inferior hypogastric plexus, and Frankenhauser's plexus) and the hypogastric nerves simultaneously with a single device.

The device may also have bilateral pairs of electrodes: right and left anterior, right and left anterior-lateral, right and left posterior-lateral, and right and left posterior leads. Any individual electrode or grouping of electrodes may be programmed to work with or independently of any other electrode or grouping of electrodes as described in further detail below. Bilaterality allows great flexibility of use. Each patient has an individual distribution of autonomic nerves and plexuses and some may have a dominant side. Alternating between right and left sides may also be important for any given patient to reduce habituation. Stimulation regimens may be customized for each patient.

The position of the device is essential to its unique ability to stimulate the target autonomic plexuses in the pelvis. For example, the posterior electrodes are adjacent to the IHP, the posterior-lateral electrodes are adjacent to left and right Frankenhauser's plexuses, the anterior electrodes are adjacent to the vesical plexus and the anterior-lateral electrodes are adjacent to the fibers approaching and leaving the vesical plexus. The anterior-lateral electrodes and posterior-lateral electrodes may ultimately reside adjacent to the vesical plexus or IHP respectively, depending on normal variant distribution of nerves and plexuses in an individual patient. As noted above, some IHP or hypogastric nerve fibers may travel along the undersurface of the cardinal ligament, just anterior to the USL. The posterior or posterior-lateral sets of electrodes may stimulate the autonomic fibers in the IHP or nerve fibers leaving or approaching the IHP that affect autonomic communication with the middle rectal plexus and/or autonomic rectal nerves. They may also affect signaling of the left and right hypogastric nerves as they approach and leave the IHP along the distal end of the uterosacral ligaments USL.

There will be multiple embodiments that optimize the direction of signal to the target structures and/or contact with the tissue. For example, in an embodiment the ring will have a flared and/or curved rim to increase electrode contact with the vaginal wall and adjacent nerves. Another embodiment may have protruding tabs extending from the ring to maintain position and/or more effectively direct current to the target nerves or plexuses. The device may also have a marker or positioning feature in order to maintain proper orientation relative to a midline. There may also be a feature available to optimize the transmission of electrical signal across the vaginal wall.

By directing signals to the peri-cervical plexuses and nerves, stimulation is directed to autonomic nerves while minimizing, and possibly eliminating, stimulation of somatic nerves and pelvic floor muscles. This is an essential distinction of the present invention from current devices. Because the device will reside in the fornices, or uppermost portion of the vaginal apex in some women, it will be well proximal to the somatic sensory nerve distribution. This will allow the patient to wear the device without awareness, making continuous treatment regimens possible. Such continuous regimens may be difficult with conventional devices residing lower in the vagina. Convenience of use, privacy, and comfort may increase compliance and, therefore, treatment success using the devices and methods of the present invention.

The device being described is able to work unilaterally, bilaterally, anteriorly, posteriorly and/or laterally as a single device that is easily placed and removed. With the device of the present invention the stimulation sites may also be changed or rotated. For example, a stimulation regimen may alternate between the rightward then leftward aspect of the IHP or vesical plexus, right and left Frankenhauser's plexus, or the junction or intersection between the right and left hypogastric nerves and the IHP. The feature allows increased flexibility with treatment regimens, giving certain plexuses or nerves rest while stimulating others.

The device of the present invention will also be able to target vastly more autonomic signals traveling to and from the pelvis. This may make it more effective at treating global pathologic problems, such as chronic pelvic pain. For example, a patient with severe pelvic pain may require continuous circumferential stimulation while a patient with overactive bladder may only need to target therapy to a single plexus.

As such, the device of the present invention permits the patient to receive individualized therapy. After initial placement, each patient's symptoms, response to treatment and any side effects may be monitored. A regimen will be customized based on her response to therapy. The device is programmable and the patient will be able to have adjustments to her regimen as desired. The plurality and laterality of electrodes allows a wide variety of stimulation opportunities.

For example, an overactive bladder patient may do well with the electrodes adjacent to the IHP stimulating 30 minutes daily. A patient with side effects to signaling of the IHP, say constipation, may prefer use of the anterior leads near the vesical plexus. If a patient has a blunted response after a long course of use, a good option could be to stimulate only the right anterior leads for a week and then rest the associated nerves while stimulating the leftward nerves of the vesical plexus during the following week. An interstitial cystitis/painful bladder syndrome patient may benefit from stimulating the vesical plexus and one or both of Frankenhauser's plexuses simultaneously to treat both bladder pain and urgency.

A patient with a spinal cord injury may do better with signaling the IHP continuously to control high levels of aberrant signal. This could afford treatment of fecal and urinary incontinence. Another patient may benefit from activating Frankenhauser's to treat non-obstructive urinary retention.

A woman suffering from dysmenorrhea (pain with menstruation) may only need the posterior-lateral leads active in order to stimulate Frankenhauser's plexuses and avoid dampening signal to and from the rectum or bladder. She could use the device five days a month. One patient with chronic pelvic pain may require continuous circumferential stimulation. Another may only require therapy targeted to the plexuses on one side allowing the rectal and bladder signals to function normally on the contralateral side. One therapeutic goal will be to find the least amount of signal required to treat each patient.

Specific aspects of the present invention are now described. The device has a nerve stimulating element positioned on an exterior surface of a body for contact with the exposed or internal surface of the vagina. The nerve stimulating element may stimulate nerves in any suitable manner including provision of one or more emitting elements, which emit electrical energy, ultrasound energy, a drug, a magnetic field or other suitable stimulus. In a specific embodiment, the nerve stimulating element may be one or more electrodes, which deliver electrical energy to stimulate adjacent plexuses, nerves and associated autonomic nerve fibers.

As mentioned above, many conventional devices contribute to side effects from stimulating somatic nerves adjacent to the distal or lower half of the vagina. These devices also often describe intentionally stimulating pelvic muscles and somatic nerves. The present invention avoids drawbacks associated with these devices by providing a device which has all of the nerve stimulating elements positioned in the proximal half of the vagina and may have the entire device positioned in the proximal half of the vagina. To this end, the present invention provides nerve stimulating elements that are positioned close to the target plexuses. These nerves travel close to the proximal end of the vagina and have branches, which are typically no more than 2 cm from the exposed surface of the vagina and, as such, the preferred embodiments are described with the nerve stimulating element being no more than 3 cm from the target nerve plexus or nerve. Stated another way, the nerve stimulating element may be positioned no more than 3 cm from the uterosacral ligaments which are positioned adjacent the target plexuses. Stated still another way, the nerve stimulating element is positioned to stimulate the vesical plexus, left and right Frankenhauser's plexus, left and right hypogastric nerves, and/or inferior hypogastric plexus without intervening nerves, and in particular without intervening somatic nerves. Stated still another way, the nerve stimulating element may be positioned to contact the exposed surface of the vagina closer to the left or right hypogastric nerve, vesical plexus, Frankenhauser's plexuses, or the inferior hypogastric plexus, than to the pelvic floor. Stated yet another way, the nerve stimulating element (and in some embodiments all nerve stimulating elements) is positioned within 3 cm from a proximal end of the vagina, proximal to a distal end of the cervix, or proximal to the midpoint between the proximal and distal ends of the vagina. Finally, the entire device may be positioned proximal to a midpoint between the proximal and distal ends of the vagina or within 5 cm from the proximal end of the vagina.

The device may also include a plurality of nerve stimulating elements to stimulate the left and right sides of the target nerve plexuses and/or nerves either simultaneously or independently. Providing independent nerve stimulating elements on the left and right sides of the target plexuses and nerves permits tailoring the therapy for the user and condition being treated. Furthermore, the laterality of treatment regions may be changed periodically to reduce habituation thereby permitting stimulation of the same plexus from different approaches.

The body of the device may form a closed loop having a central opening with the cervix positioned in the central opening. Although the body extends completely around the cervix, the body may extend only partially around the cervix. To this end, the body may extend around at least 120 degrees, or even 270 degrees, around the cervix relative to the cervical axis. For example, the body may be C-shaped or U-shaped. In another aspect of the present invention, the nerve stimulating elements (such as the electrodes) are spaced apart at least 120 degrees, or even 180 degrees, relative to the cervical axis (or the central axis when the cervix is absent) so that the target nerve plexuses may be stimulated independently (or simultaneously) as described herein with a single device on opposite sides of the cervix. Of course, the nerve stimulating element(s) may be positioned only along a posterior or anterior half of the vaginal canal for targeted use as described herein rather than spaced around the periphery of the device.

The present invention may be used to treat any one or more of the following conditions: urinary urgency, frequency, nocturia, urge incontinence, stress incontinence of urine, loss of urine without sensory awareness, overflow incontinence, bladder pain, urethral pain, urethral syndrome, urethral stricture, urinary hesitancy, protracted urinary stream, pelvic floor dyssynergia, interstitial cystitis, dysuria, overactive bladder, incomplete bladder emptying, urinary retention, hesitancy, dysmenorrhea, pelvic pain, pelvic venous congestion syndrome, endometriosis, irritable bowel syndrome, constipation, fecal urgency, fecal incontinence, rectal pain, pain with defecation, anal pain. Of course, numerous aspects of the present invention may be practiced for a different condition without departing from the scope of the invention.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 18 shows an end of the hub that abuts against the battery.

FIG. 19 shows another end of the hub that is coupled to the control system.

DETAILED DESCRIPTION

Figure 1:
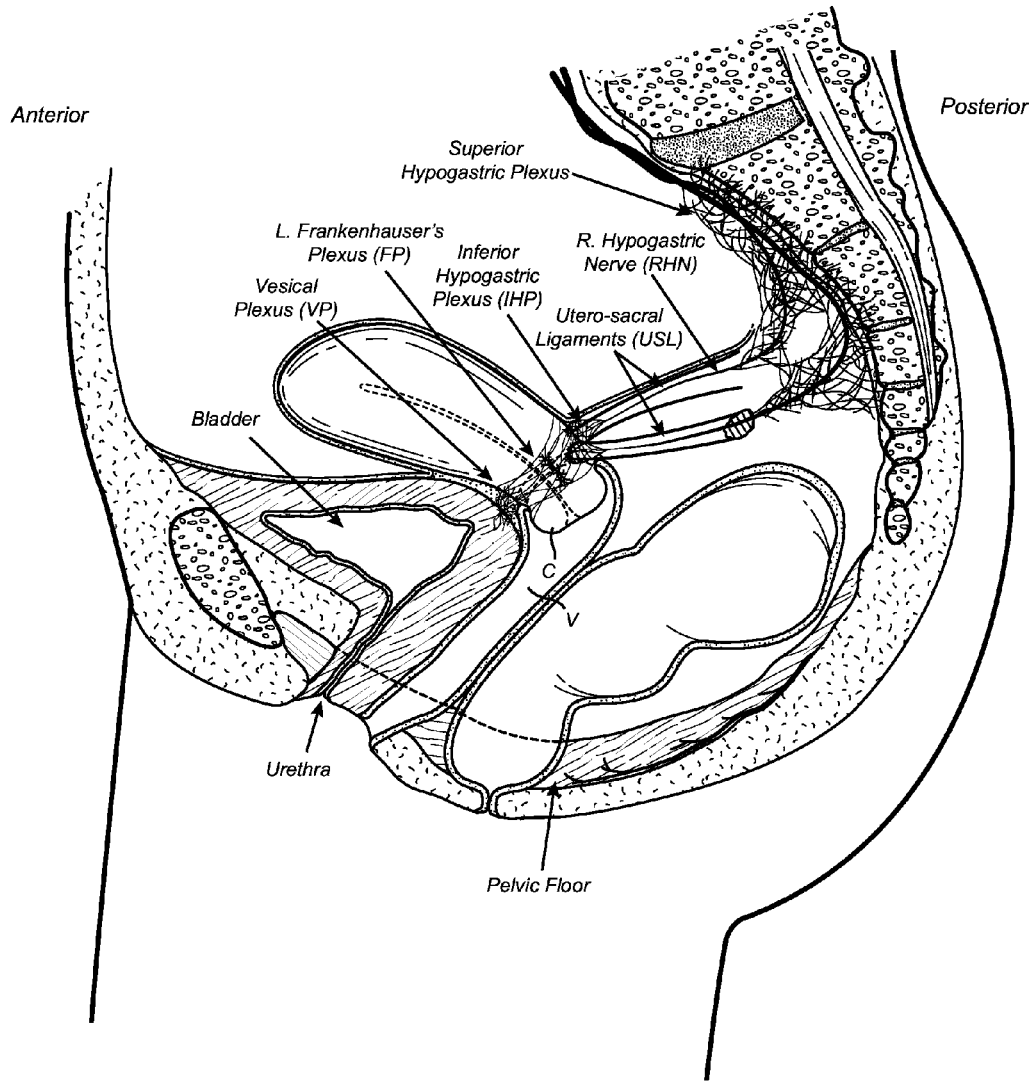
FIG. 1 is a parasagital view into the female pelvis from the left.
Figure 2:
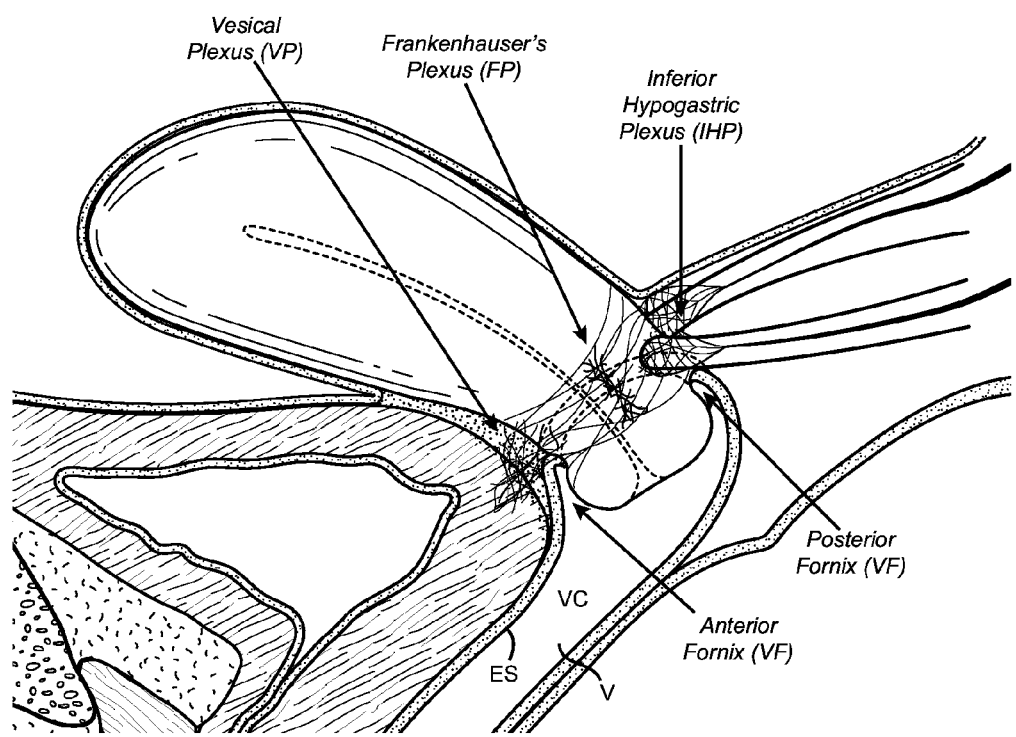
FIG. 2 is an enlarged view of the upper vagina and uterus.
Figure 3:
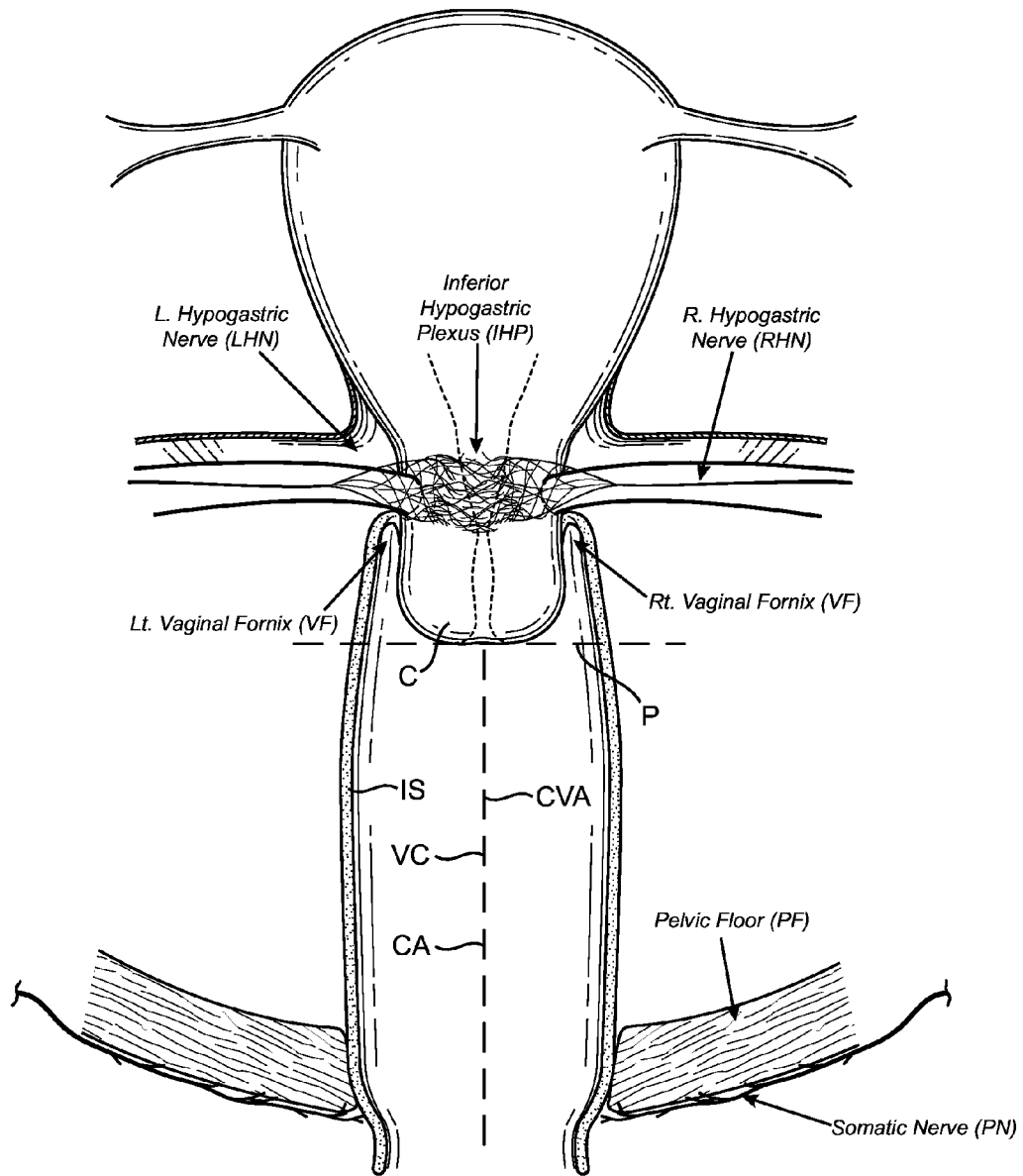
FIG. 3 is a posterior view of the gynecologic organs.
Figure 4:
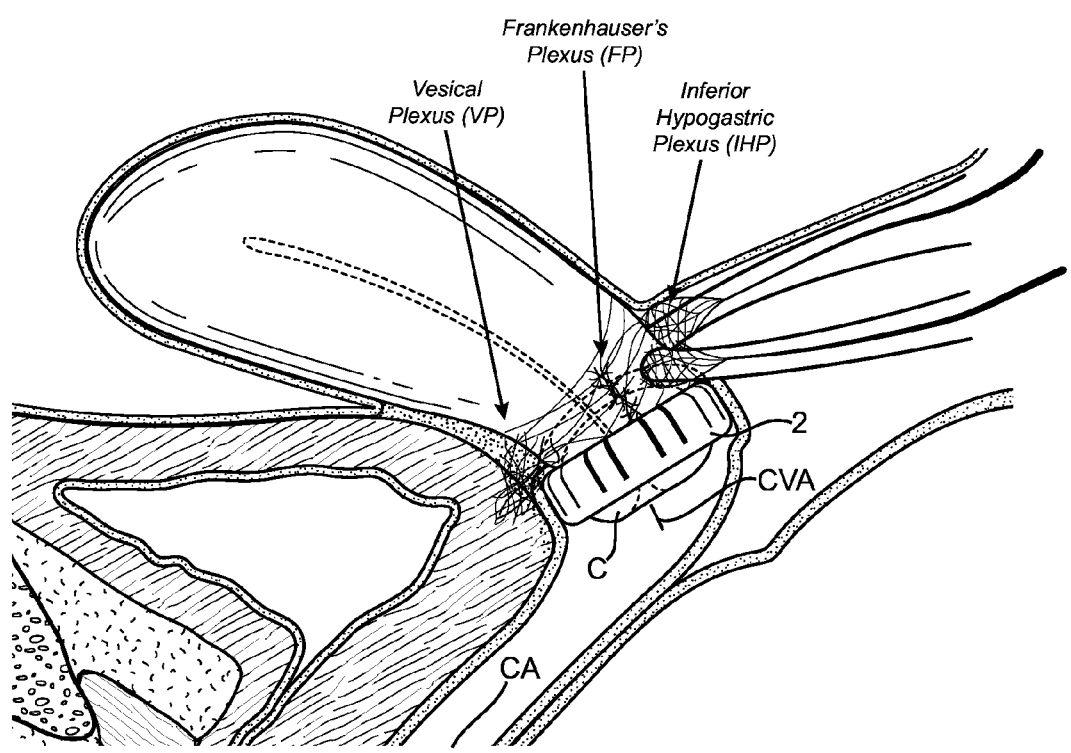
FIG. 4 is an enlarged view of the upper vagina and uterus with the device of the present invention positioned in the vaginal fornices.
Figure 5:
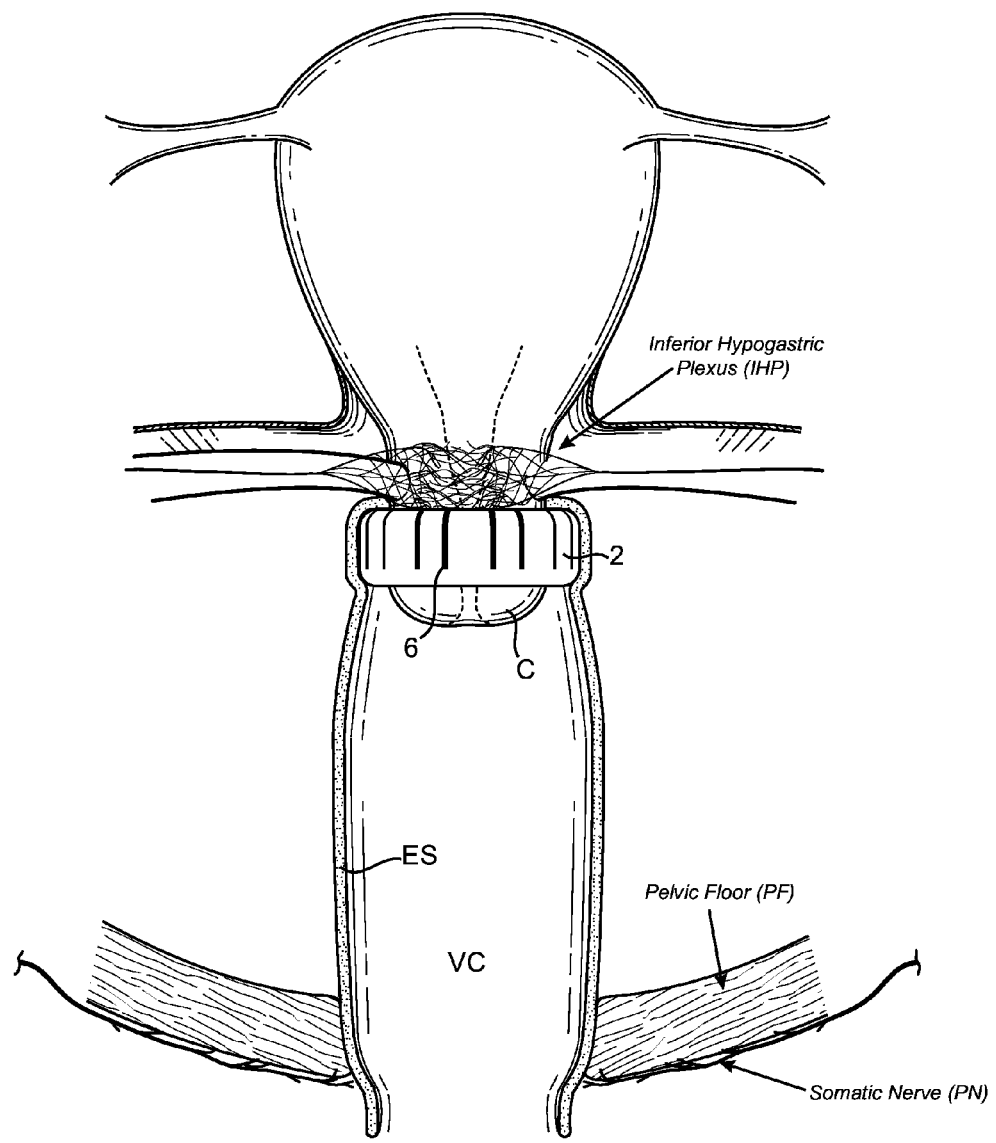
FIG. 5 is a posterior view of the gynecologic organs with the device positioned in the vaginal fornices.
Figure 6:
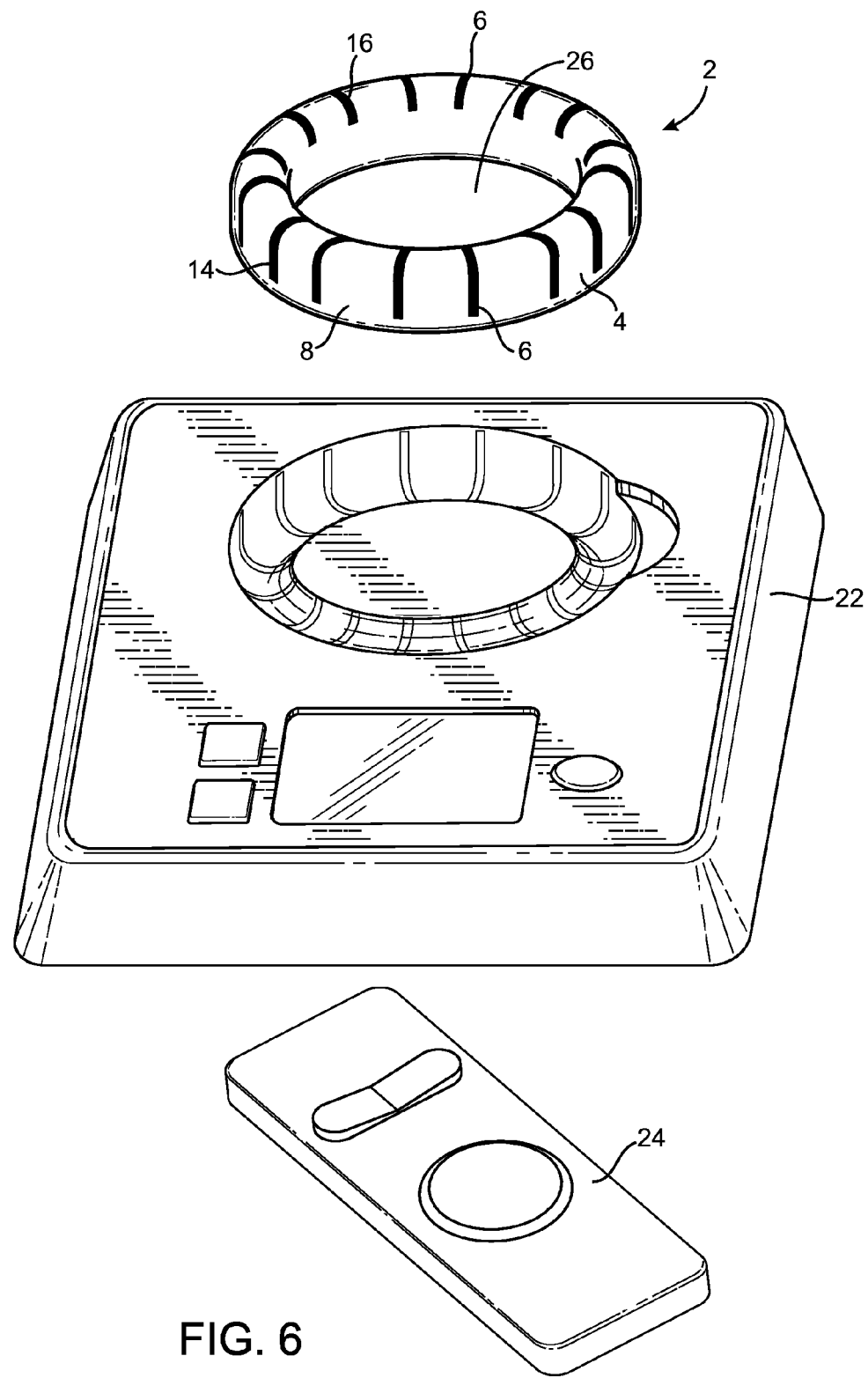
FIG. 6 shows the device, a charger and a controller.
Figure 7:
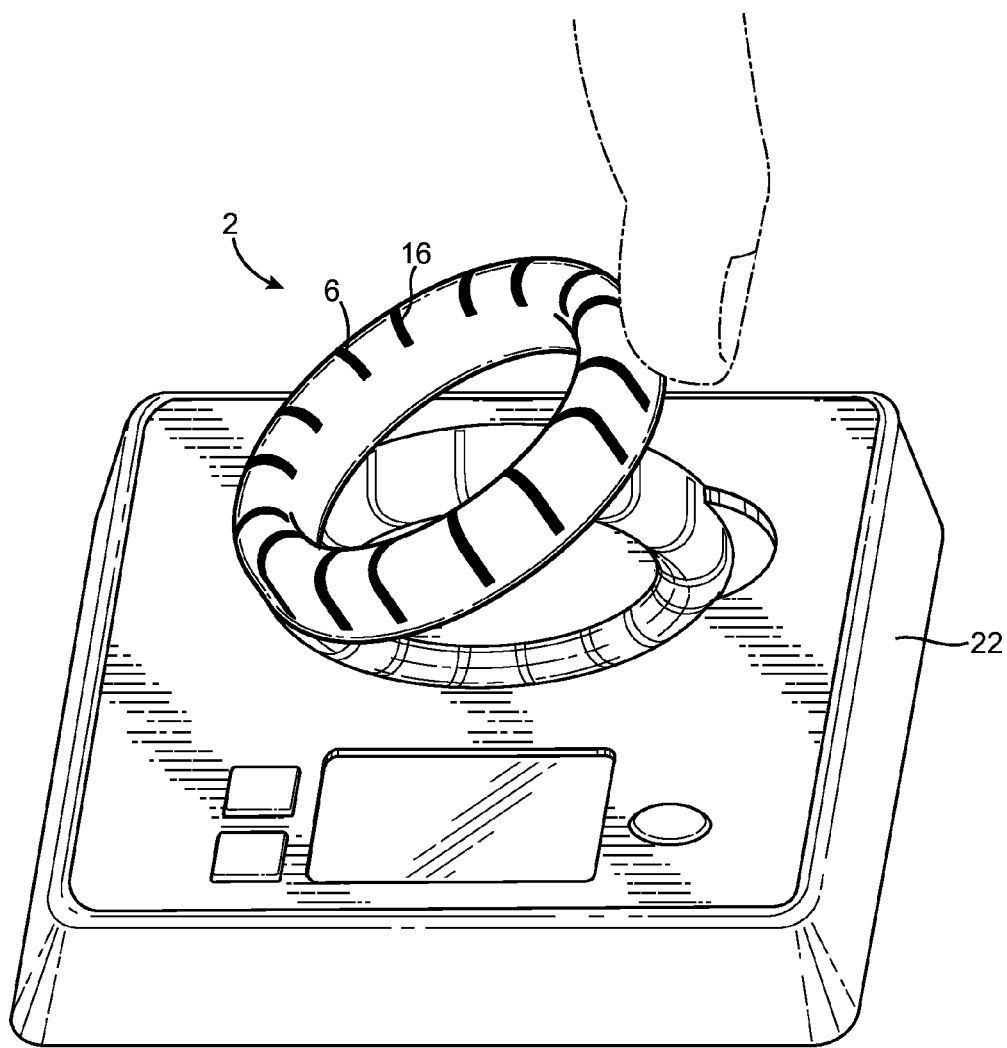
FIG. 7 shows removal of the device from the charger.

For the purpose of defining the invention, various terms are now defined for use herein with reference to FIGS. 1-3. Firstly, the vagina V is a fibroelastic, muscular structure that forms a canal (hereinafter "vaginal canal" VC) having a distensible, flexible lining. The surface of this flexible lining has an internal or exposed surface ES. The vagina, and vaginal canal, as defined herein has a proximal end terminating at the proximal aspect of the cervix and a distal end at the introitus where it joins the vulva. If the cervix C has been removed or is congenitally absent, the proximal end of the vagina (and vaginal canal) is simply defined by the uppermost portion of the vagina, also known as the vaginal cuff.

As used herein, the shape of the vaginal canal VC defines a central axis CA. A cervical axis CVA extends through and is aligned with the cervical canal CC. The cervical axis CVA is also an axis of symmetry, as closely as can be approximated with the anatomy, for the cervix extending through the cervical opening or cervical canal. A midpoint between the proximal and distal ends of the vagina (or the vaginal canal) is determined herein using the midpoint of the central axis. The central axis CA may, of course, have a relatively complex shape so long as the central axis CA generally defines and follows the orientation and shape of the vaginal canal VC. The proximal end of the vagina (and vaginal canal) is defined by the uppermost portion of the vagina. For example, a proximal portion of the vagina or vaginal canal extending 3 cm from the proximal end of the vagina includes the vagina extending 3 cm from the uppermost (proximal) end.

The vaginal fornices VF, as used herein, refers to a space or recess between the cervix and the adjacent vaginal wall. Specifically, the space is positioned between the exposed surface ES of the vaginal canal VC and an exposed surface of the cervix C and further bounded by a plane P extending perpendicular to the cervical axis CVA and passing through distal end of the cervix C. The vaginal fornices VF may be thought of as a somewhat torus-shaped space but, of course, varies from patient to patient.

Referring now to FIGS. 4-8, a device 2 in accordance with the present invention is shown. The device 2 includes a body 4 having a plurality of nerve stimulating elements 6 positioned on an exterior surface 8 of the body 4 for contact with the exposed or internal surface ES of the vaginal wall 12. The nerve stimulating elements 6 may stimulate nerves in a number of different ways without departing from numerous aspects of the invention. For example, the nerve stimulating element 6 may include one or more emitting elements 14 which emit electrical energy, ultrasound energy, a drug, a magnetic field or other suitable stimulus to the target nerves.

In a specific embodiment, the nerve stimulating elements 6 may be one or more electrodes 16 that deliver electrical energy to stimulate adjacent nerves as described below. As used herein, it is understood that use of "electrode" or "emitting element" herein shall be interchangeable with the term nerve stimulating element, and vice versa, as applicable. Thus, aspects of the invention described or claimed specifically in relation to the electrodes 16 or nerve stimulating element 6 are equally applicable to the other and such substitution is expressly incorporated here. Furthermore, the application of electrical stimulus is sufficient to change the signals transmitted by the target nerves and plexuses described below. In this manner, neuromodulation of the target nerves is achieved.

The electrodes 16 are coupled to a control system 18 which in turn is coupled to a power source 19 such as a battery 20. The device 2 may include a battery charger 22 or may be charged transcutaneously as is known in the art. Of course, an advantage of the present invention is that the device 2 may easily be removed, charged and repositioned which cannot be accomplished with conventional surgically placed devices. The device 2 may also include an external controller 24 which may operate the device remotely when the device 2 is in place. The battery charger 22 may also be a controller for programming the device 2 in accordance with methods described herein. A few prior art devices which describe suitable control systems, controllers and battery charging systems are described in U.S. Pat. Nos. 7,729,772, 7,813,809 and 8,165,692 which are hereby incorporated by reference. The controller 24 (and charger 22) may control the duration, frequency, intensity and stimulation protocol as described herein and in the patents incorporated above.

Figure 21:
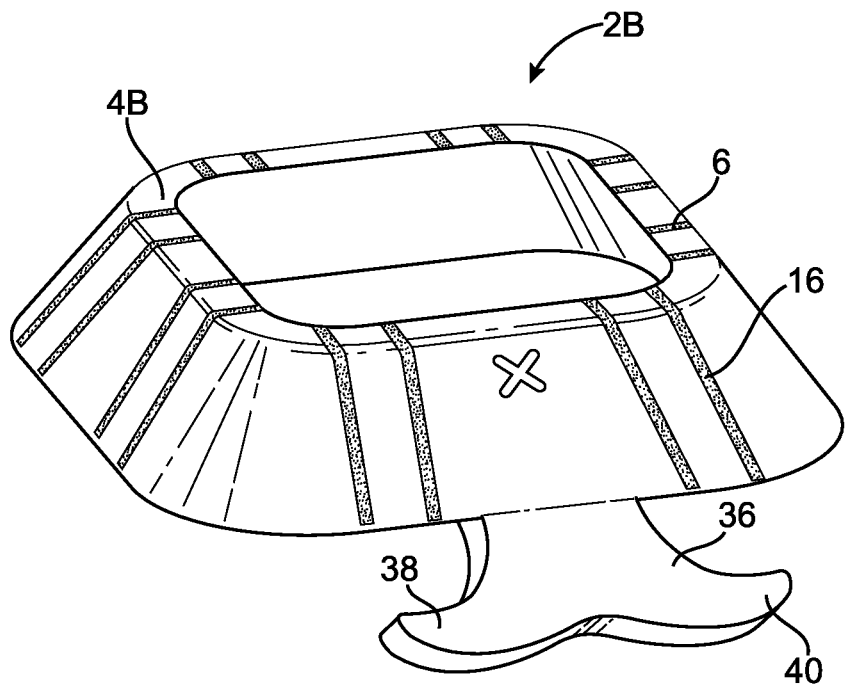
FIG. 21 shows still another device in accordance with the present invention.

The body 4 of the device 2 forms a closed loop having a central opening 26 with the cervix C positioned in the central opening 26. The body 4 may be substantially circular or may have substantially straight sides 28 as shown in FIG. 21. Of course, the body 4 may take any other shape such as oval, elliptical, square, or even hexagonal. Although the body 4 extends completely around the cervix, the body 4 may extend only partially around the cervix. To this end, the body 4 may extend around at least 180 degrees, or at least 270 degrees, around the cervix relative to a cervical axis 30 and may be, for example, C-shaped, V-shaped or U-shaped. As used herein, the central opening 26 does not need to be completely surrounded by the body 4 so long as the body 4 extends partially around the cervix and opening 26 as described herein. Thus, a substantially C-shaped or U-shaped body still will include a central opening 26 with each central opening 26 defining a central axis of the body 4 CAB. The nerve stimulating elements 6 (such as the electrodes 16) are also spaced apart at least 120 degrees, or even 180 degrees, relative to the cervical axis CVA (or the central axis of the body CAB described further below when the cervix is absent) so that the various nerve plexuses may be stimulated as described herein. Of course, the nerve stimulating element(s) 6 may be positioned only along a posterior or anterior half of the vaginal canal for targeted use as described herein without departing from numerous aspects of invention.

The device 2 of the present invention may be positioned partially or entirely within the vaginal fornices VF. The nerve stimulating element 6 (and in some embodiments all of the nerve stimulating elements 6) contacts the exposed surface of the vagina 10 proximal to the distal end 46 of the cervix.

Figure 8:
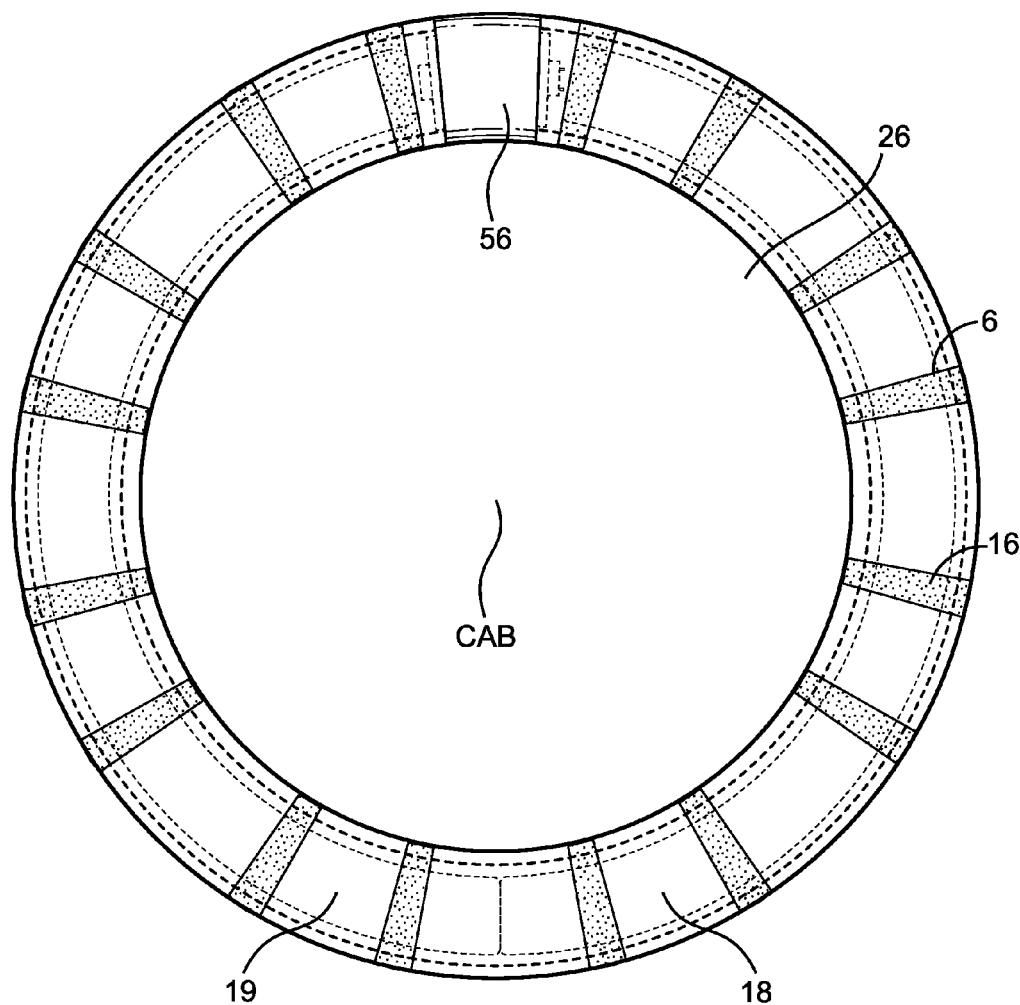
FIG. 8 is a top view of the device showing the electrodes.
Figures 14A, 14B:
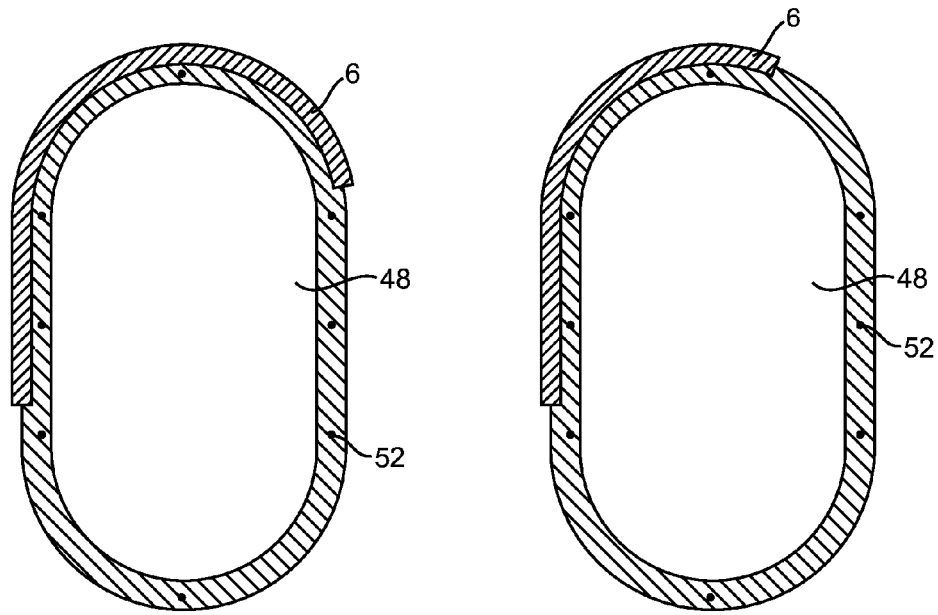
FIG. 14A is a cross-sectional view of the body.
FIG. 14B is another cross-sectional view of the body with an alternative electrode.
Figures 15A, 15B:
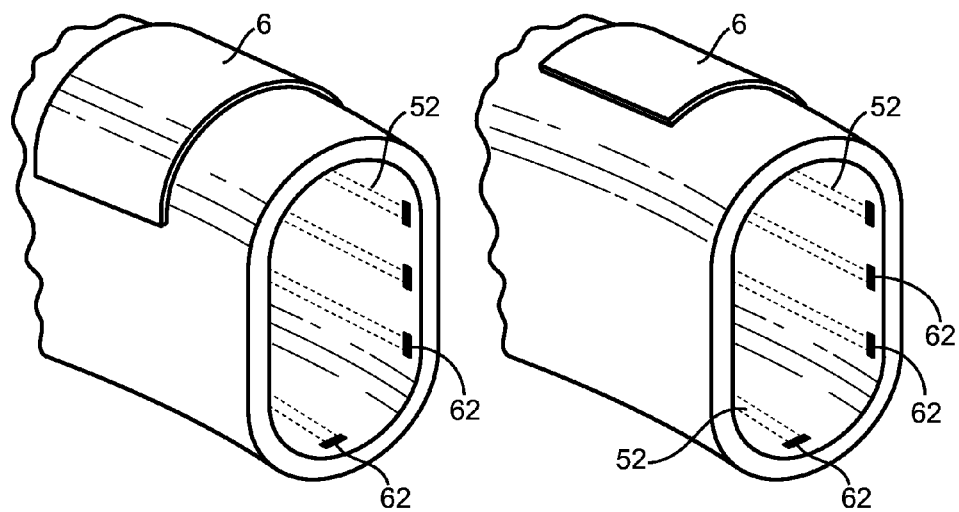
FIG. 15A is a perspective view of one end of the body.
FIG. 15B is a perspective view of the same end of the body as FIG. 15A with the alternative electrode of FIG. 14B.
Figure 16:
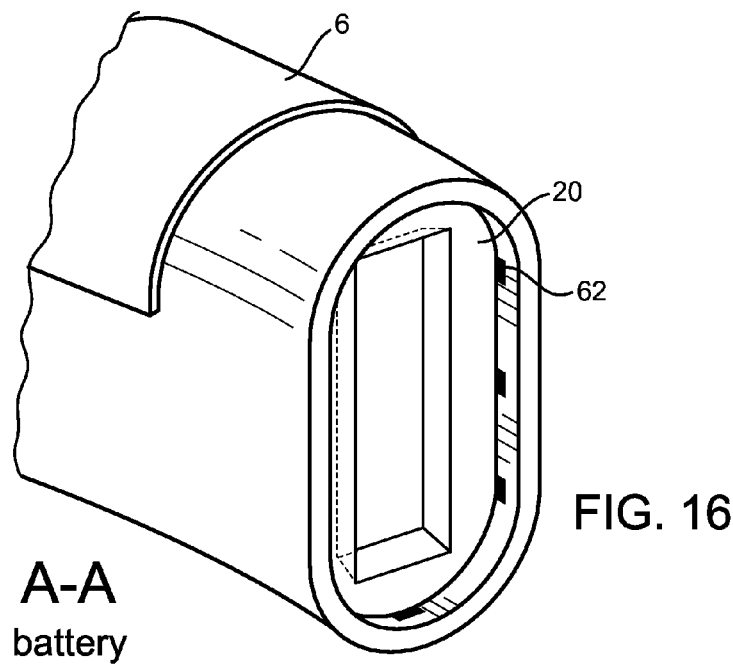
FIG. 16 is a perspective view of the end of the body with the battery positioned in the body.

The body 4 has an elongate cavity 48 (see FIGS. 14A and 14B) in which the control system 18 and the battery 20 are positioned as shown in FIG. 8. The battery 20 and control system 18 are directly coupled together. The electrodes 16 are coupled to the control system 18 with a wire 52 (or other suitable conductive element) electrically coupled to each of the electrodes 16. The wires 52 extend through a sidewall 54 of the body 4 and are directed toward a hub 56 which electrically couples each of the wires 52 to the control system 18. The hub 56 is positioned between a first connector 58 and a second connector 60. Half of the wires 52 are directed to each of the first and second connectors 58, 60 (eight wires 52 for each of the connectors 58, 60 in the preferred embodiment of FIG. 8). The wires 52 terminate at wire contacts 62 which are used to electrically couple the wires 52 to the hub 56 and, in turn, to the control system 18 as now described. Referring to FIGS. 14A and 15A, the electrode 16 may wrap around from a radially outer surface 53 to a radially inner side 55. An alternative electrode 57 is shown in FIGS. 14 B and 15B in which the electrode 57 does not wrap around to a radially inner side 59 thereby potentially minimizing stimulus transmitted through the cervix. All features, devices, embodiments and methods described herein may use either the electrode 16 or electrode 57.

Figure 13:
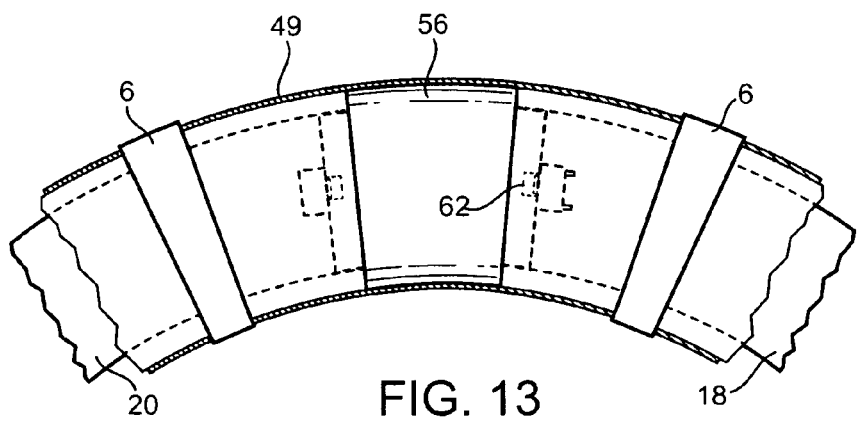
FIG. 13 shows a layer applied over the body to seal the battery and control system within the body.
Figure 17:
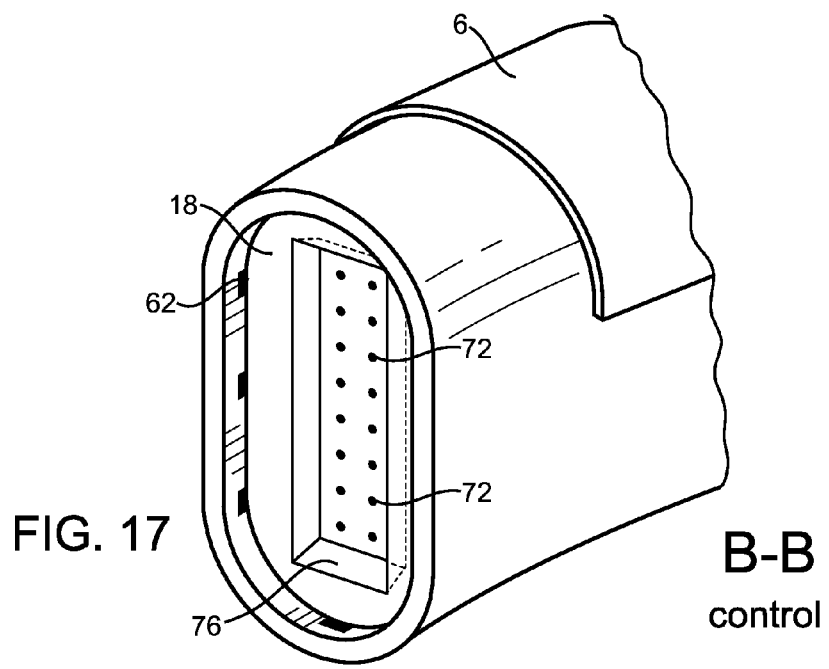
FIG. 17 is a perspective view of the end of the body with the control system positioned in the body.

Referring to FIGS. 10-19, the hub 56 has a protrusion 64 on each end that fits within the cavity 48 in the body 4. The protrusion 64 on the battery 20 side abuts directly against the battery 20 (see FIGS. 16 and 18) and the other protrusion 64 abuts against the control system 18 (see FIGS. 17 and 19). The protrusion 64 includes hub contacts 66 on a radially outer wall that are aligned and electrically coupled to the wire contacts 62 at each of the first and second connectors 58, 60. Wires (not shown) leading from the hub contacts 66 are directed through the hub 56 to the control system 18. Each of the wires terminates at an electrical connector 70 (FIG. 19) that engages electrical connectors 72 on the control system 18 (FIG. 17). The electrical connectors 72 may be formed on a first extension 74 of the hub 56 that forms a snap fit connection with a recess 76 in the control system 18. A second extension 77 on the other side of the hub 56 may form a snap fit connection with the battery 20 (FIG. 18). Of course, the device 2 may prevent access to the battery 20 and control system 18 rather than providing the snap fit connection. For example, the entire device 2 may be encased in a polymer 49 to remove spaces and voids and to seal all connections to the hub 56 while leaving the electrodes 16 exposed as shown in FIG. 13.

Figure 9:
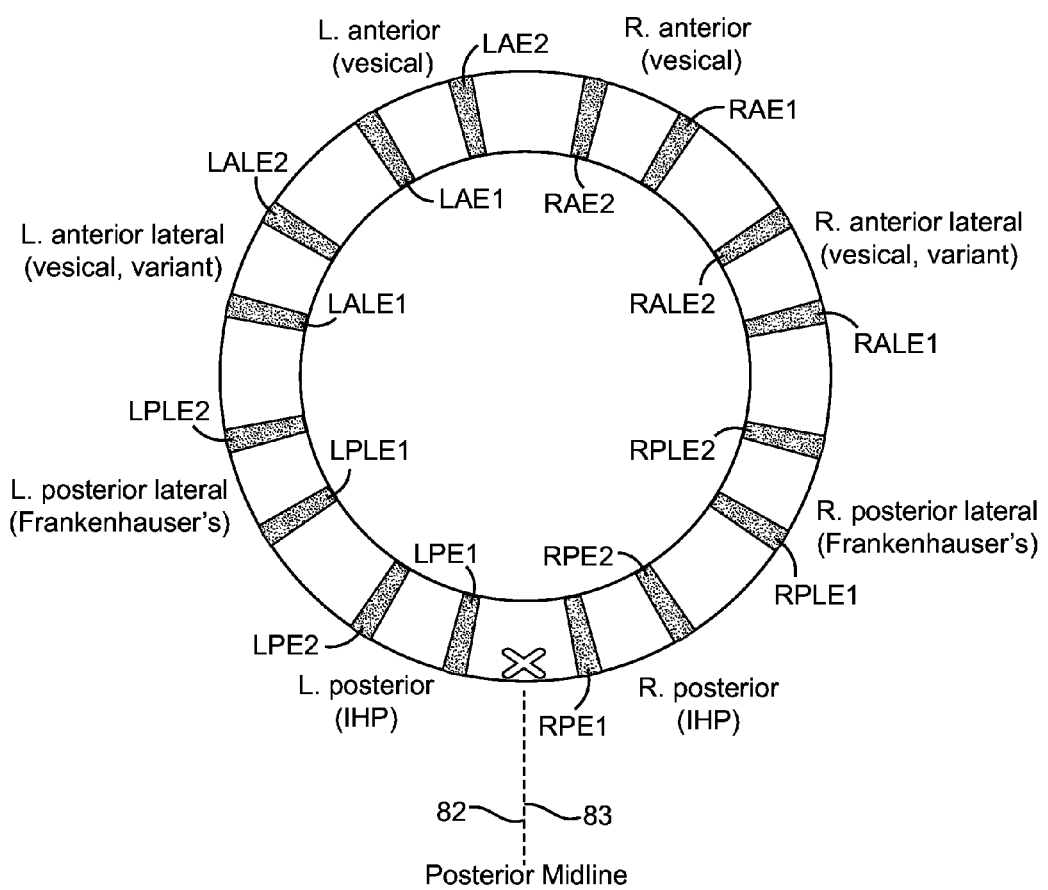
FIG. 9 shows the orientation of the electrodes.
Figure 10:
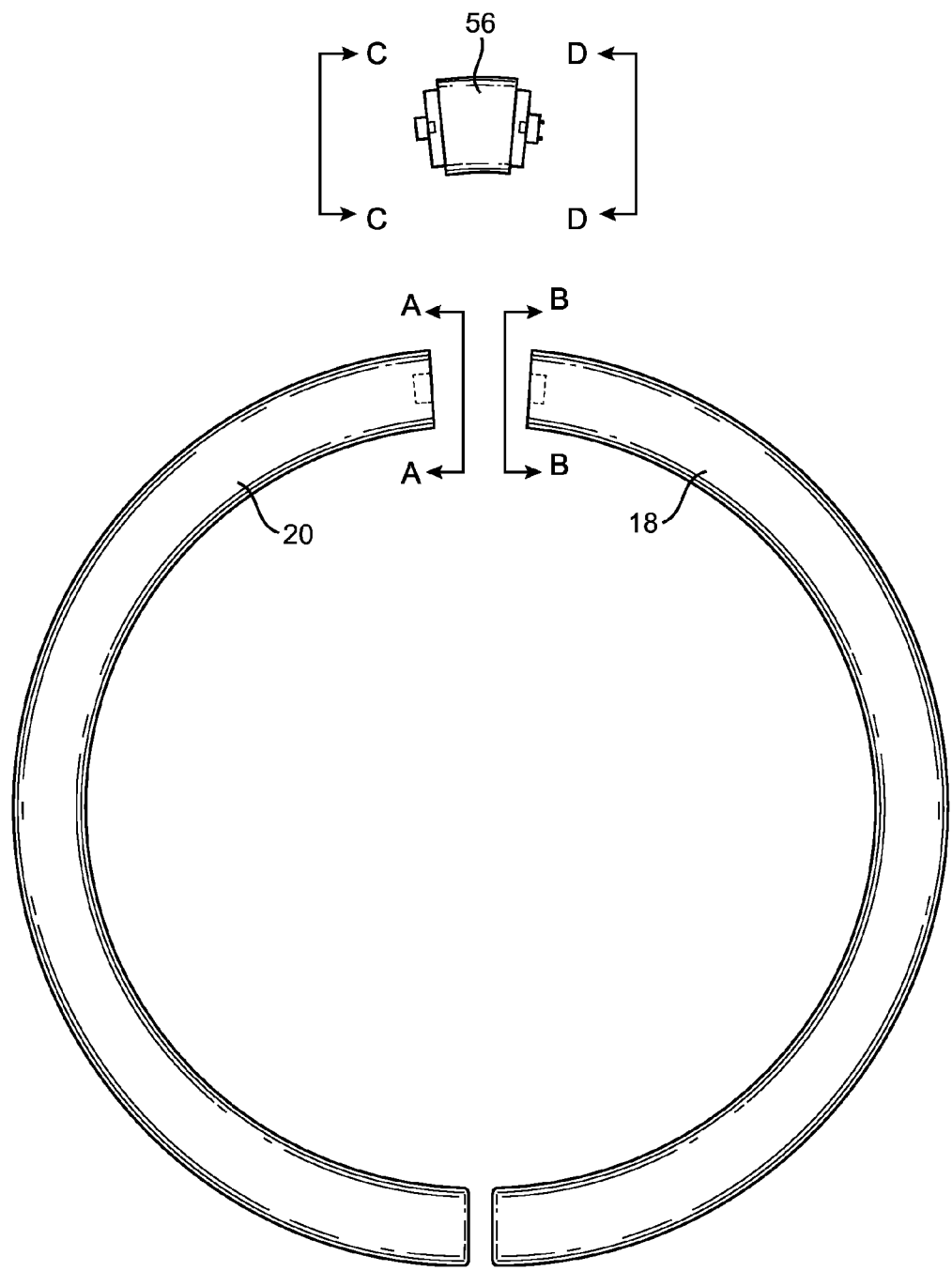
FIG. 10 shows a battery, control system and hub, which interconnects the control system with the electrodes.
Figure 11:
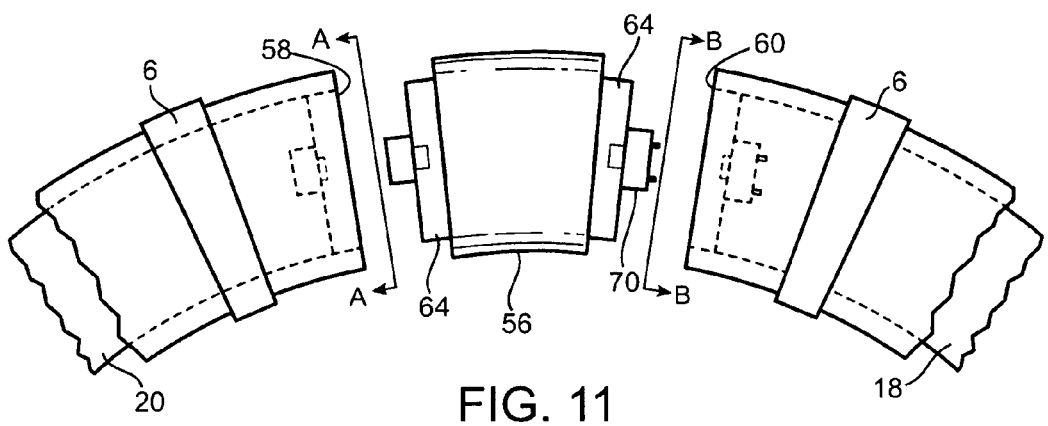
FIG. 11 is an exploded view of the hub, battery and control system.
Figure 12:
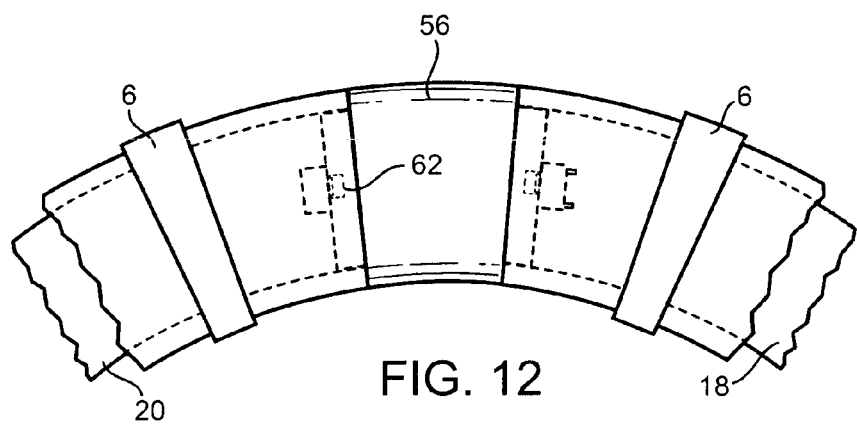
FIG. 12 shows the hub connected to the battery and control system.

Referring now to FIG. 9, the electrodes 16 may be paired together to stimulate a specific nerve plexus, and even a specific side of the plexus, as now described. The device 2 includes a marker 80 to orient the device 2 along a midline 82 which generally corresponds with a midline 83 of the user. Adjacent the marker 80 is a left posterior electrode pair LPE1, LPE2 and a right posterior electrode pair RPE1, RPE2. The left and right posterior electrode pairs are positioned to lie adjacent to the left and right sides of the inferior hypogastric plexus. A left posterior lateral electrode pair LPLE1, LPLE2 and a right posterior lateral electrode pair RPLE1, RPLE2 are positioned to lie adjacent the left and right Frankenhauser's plexuses, respectively. Finally, the vesical plexus may be targeted on the left side with a left anterior lateral electrode pair LALE1, LALE2 and a left anterior electrode pair LAE1, LAE2 while the right side of the vesical plexus may be stimulated with a right anterior lateral electrode pair RALE1, RALE2 and a right anterior electrode pair RAE1, RAE2. Thus, the present invention may be useful in stimulating the same plexus from the right side and the left side simultaneously, independently and/or at different times. Of course, the user may only actuate the left or right side rather than alternating sides for stimulation if the therapy is better tolerated or more successful on one side or the other. The control system 18 may change the laterality periodically such as every few days.

Although the above description presents distinct electrode 16 pairings, it is understood that any of the electrodes 16 may be grouped together by the control system 18 for generating nerve stimulus. For example, the two electrodes 16 on opposite sides of the marker 80 may be used to stimulate the inferior hypogastric plexus along the midline 82 rather than preferentially on the left or right sides. In another example, the left hypogastric nerve (and the junction of this nerve and the IHP) may be stimulated using the LPE2 and the LPLE1 electrodes while the right hypogastric nerve (and the junction of this and the IHP) may be stimulated using the RPE2 and the RPLE1 electrodes. Although the independent stimulation of different regions of the same plexus has been described with respect to left and right sides of the midline of a particular target plexus, the stimulation may take place at any two different regions of the same plexus rather than simply left and right sides as described in further detail below.

Although only one electrode 16 is used on each side of the circuit described above, two or more electrodes 16 may be used to create either side of the electrical circuit rather than using only one for each side as described above. In another aspect of the present invention, the device 2 may include at least twelve electrodes 16 and in the preferred embodiment sixteen electrodes 16. The nerve stimulating element 6 may be formed by any two electrodes 16 (or groups of electrodes 16) and, thus, the device 2 could easily have at least twenty nerve stimulating elements formed by sixteen electrodes 16 by grouping electrodes together, and "skipping" over one or two electrodes 16 (or more) to form the electrode pair rather than using adjacent electrodes 16 to form the pair. An advantage of forming at least twenty different nerve stimulating elements 6 the device 2 may provide greater flexibility of treatment, reduce habituation and targeting different sides of the same plexus at different times as described herein. Skipping electrodes 16 to form a particular nerve stimulating element 6 will increase a spacing between the electrodes 16 (compared to adjacent pairs of electrodes 16) thereby providing the ability to potentially alter the depth of penetration of the stimulus. The control system 18 is configured to independently actuate each of the nerve stimulating elements 6. In this manner, the device 2 of the present invention may operate in at least twenty different modes with each mode being represented by a distinct nerve stimulating element 6 formed by a unique group of electrodes 16 in any manner described herein. Thus, the present invention not only is able to target numerous plexuses with a single device but each of these plexuses may be stimulated in a variety of independent modes. For example, the IHP may be stimulated with the four posterior electrodes 16 (LPE1, LPE2, RPE1, RPE2) in at least four modes (or stated another way by forming at least four different nerve stimulating elements) to stimulate the IHP. In fact, the four posterior electrodes 16 may form at least eight different modes (or stated another way by forming at least eight different nerve stimulating elements 6) to stimulate the IHP by simply grouping electrodes 16 in the manner described herein (adjacent pairs, skipping one, skipping two, grouping two or more electrodes on one side of the circuit or on both sides of the circuit). In this manner, different regions or portions of the same plexus may be stimulated. Of course, the regions stimulated will have overlapping portions but use of different electrode 16 configurations described herein will create different stimulus patterns and regions. Although the device 2 of the present invention may form numerous independent nerve stimulating elements 6, simultaneous actuation may produce fewer nerve stimulating elements 6 (such as eight when using sixteen electrodes 16), nevertheless, the device 2 still may form far more nerve stimulating elements 6 for independent actuation as described herein. The nerve stimulating elements 6 are also preferably formed by more than mere modification of power, frequency or another parameter for the same nerve stimulating element 6. As such, the nerve stimulating element 6 may each have a unique position in that the electrodes 6 are grouped, paired or otherwise organized in a unique manner for each of the nerve stimulating elements 6 formed. As such, each nerve stimulating element 6 formed has a unique position even if a grouping or pair share one or more electrodes 6 so long as the groups or pairings are not identical. Each unique position provides a different focus unlike a single nerve stimulating element that can only change power, frequency or some other characteristic while leaving the stimulation pattern substantially the same.

Although numerous nerve stimulating elements 6 may be formed with the electrodes 16 forming numerous different nerve stimulating elements, in some aspects of the invention the device 2 may have at least four, or at least eight, nerve stimulating elements 6 as described above. Each of the nerve stimulating elements 6 may be actuated independently (or simultaneously, of course) to stimulate different regions of tissue (although these regions may overlap).). In another aspect of the invention, the nerve stimulating elements 6 are advantageously distributed around the body 4 to independently stimulate the various target plexuses. To this end, the device 2 may include at least three nerve stimulating elements 6 which are angularly spaced at least 70 degrees from adjacent nerve stimulating elements relative to the cervical axis CVA or central axis of the body 4 CAB. If more regions are targeted, the device 2 may include at least four nerve stimulating elements which are angularly spaced at least 50 degrees from adjacent nerve stimulating elements relative to the cervical axis CVA or central axis of the body 4.

Although the nerve stimulating element 6 has been described with respect to pairs of electrodes 16, the nerve stimulating element 6 may be formed by a single element or even a single electrode 16 without departing from the scope of the invention. For example, a single piezoelectric element may be used to deliver ultrasound energy or the device 2 may include a single electrode 16 with the other electrode carried by another element (even an implantable element) without departing from the scope of the invention.

As mentioned above, many conventional devices introduced into the vagina suffer from the drawback that they often stimulate somatic nerves since these devices are typically positioned in the distal (lower) half of the vagina. These devices also often intend to stimulate pelvic muscles which may lead to further disadvantages described herein. The present invention avoids these drawbacks by positioning the device 2 in the proximal half of the vagina and, in some embodiments, may have all of the nerve stimulating elements 6 (or electrodes 16) in the proximal half of the vagina. To this end, the present invention provides nerve stimulating elements 6 that are positioned close to the target plexuses; the vesical plexus, left and right Frankenhauser's plexuses, the inferior hypogastric plexus and the intersection of junction between the inferior hypogastric plexus and the left and right hypogastric nerves. These nerve plexuses travel close to the proximal end of the vagina as shown in FIGS. 1-3 and typically have branches within 1-2 cm from the exposed surface ES of the vagina and, as such, the preferred embodiments are described with the nerve stimulating element 6 being no more than 3 cm from the target nerve plexus. Stated another way, the nerve stimulating element 6 may be positioned no more than 3 cm from the uterosacral ligaments which are adjacent the target nerve plexuses. Stated still another way, the nerve stimulating element 6 is positioned to stimulate the vesical plexus, Frankenhauser's plexus, or inferior hypogastric plexus without intervening nerves, and in particular without intervening somatic nerves. Stated yet another way, the nerve stimulating element 6 may be positioned to contact the exposed surface 10 of the vagina closer to the vesical plexus, left or right Frankenhauser's plexus, left and right hypogastric nerves or the inferior hypogastric plexus, than to the pelvic floor. Stated still another way, the nerve stimulating element 6 (and in some embodiments all of the nerve stimulating elements 6) is positioned to contact the exposed surface ES of the vaginal canal within 3 cm from a proximal end of the vagina or proximal to a distal end of the cervix C. The entire device 2 may be positioned proximal to a midpoint between the proximal and distal ends of the vagina. Stated another way, the entire device 2 may be positioned within 5 cm from the proximal end of the vagina. Stated still another way, the nerve stimulating elements 6 are all positioned proximal to a midpoint between the proximal and distal end of the vaginal canal.

The electrodes 16 are also oriented and organized so that they will form nerve stimulating elements 6 that will generally direct stimulus proximally. To this end, the electrodes 16, and the nerve stimulating elements 6, are organized so that a proximal surface 13 are at the same longitudinal position relative to the central axis of the body CAB and the cervical axis CA. Although the electrodes 16 and nerve stimulating elements are preferably oriented in this manner, they may be longitudinally separated without departing from numerous aspects of the present invention. For example, the electrodes 6 (and in one aspect all of the electrodes 16 or nerve stimulating elements 6) may be longitudinally spaced so that the proximal surface 13 of the electrodes 6 (and the nerve stimulating element 6 formed by the electrodes 16) relative to the central axis of the body CAB or the cervical axis CVA by no more than one cm.

Figure 20:
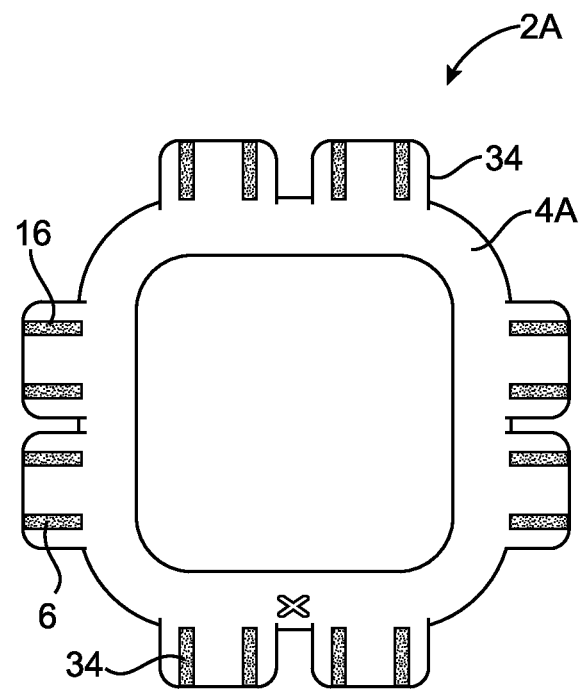
FIG. 20 shows a top view of another device in accordance with the present invention.

Referring now to FIG. 20, another device 2A is shown including a body 4A having one or more tabs 34 extending radially outward relative to a central opening 26A. The tabs 34 may help secure the device 2A in place and maintain the intended orientation of the device 2A once positioned. The electrodes 16 may be positioned on the tabs 34 so that the electrodes 16 are on the radially outer surface of the body 4A.

Referring to FIG. 21, still another device 2B is shown which has an extension 36 extending radially outward from the body 4. The extension 36 has a first curved tip 38 and a second curved tip 40 which help anchor the device 2 in position and help maintain the intended orientation. The body 2B may also be flared outwardly which also may help retention. The body 2 is flared outwardly to become larger as the body 2 extends distally in the vagina. It is understood that all of the devices 2, 2A, 2B described herein shall incorporate all methods of using the other devices 2, 2A, 2B and such use is expressly incorporated for each device described herein. Furthermore, all devices 2, 2A, 2B shall share the same inventive features described herein and such features are also expressly incorporated for all devices described herein. For example, the position and use of the electrodes 16 of device 2 shall be applicable to use of device 2A and device 2B.

The device may also be used to stimulate the vesical plexus together with either the Frankenhauser's plexus or with the inferior hypogastric plexus (or both). The vesical plexus may be stimulated independently or simultaneously with one or both of the other two plexuses. In another aspect, an anterior side may be stimulated simultaneously or independently with a posterior side.

As can be appreciated, the present invention provides the ability to target more than one plexus and, alternatively, the same plexus from a different position. For example, a plurality of nerve stimulating elements 6 are positioned to stimulate the same plexus for each of the plexuses described herein. Switching to different stimulating elements 6 may reduce habituation and/or provide other therapeutic benefits. Furthermore, the user may simply select, based on efficacy determined by the user, which of the areas is most beneficial for the particular treatment. Of course, a computer controlled algorithm may also be used to target particular areas due to set parameters or from feedback data. The control system 18 may control the device 2 to stimulate a target plexus with a first nerve stimulating element 6 for a first period of time, then stimulate the target plexus with a second nerve stimulating element 6 for a second period of time and independent of the first nerve stimulating element 6. In this manner, habituation may be addressed without changing the target plexus but changing the position of stimulation by changing the nerve stimulating element. Of course, the target plexus(es) may also be changed from any one (or more) of the target plexuses described herein to another target plexus(es) to address habituation or as otherwise desired.

Figure 22:
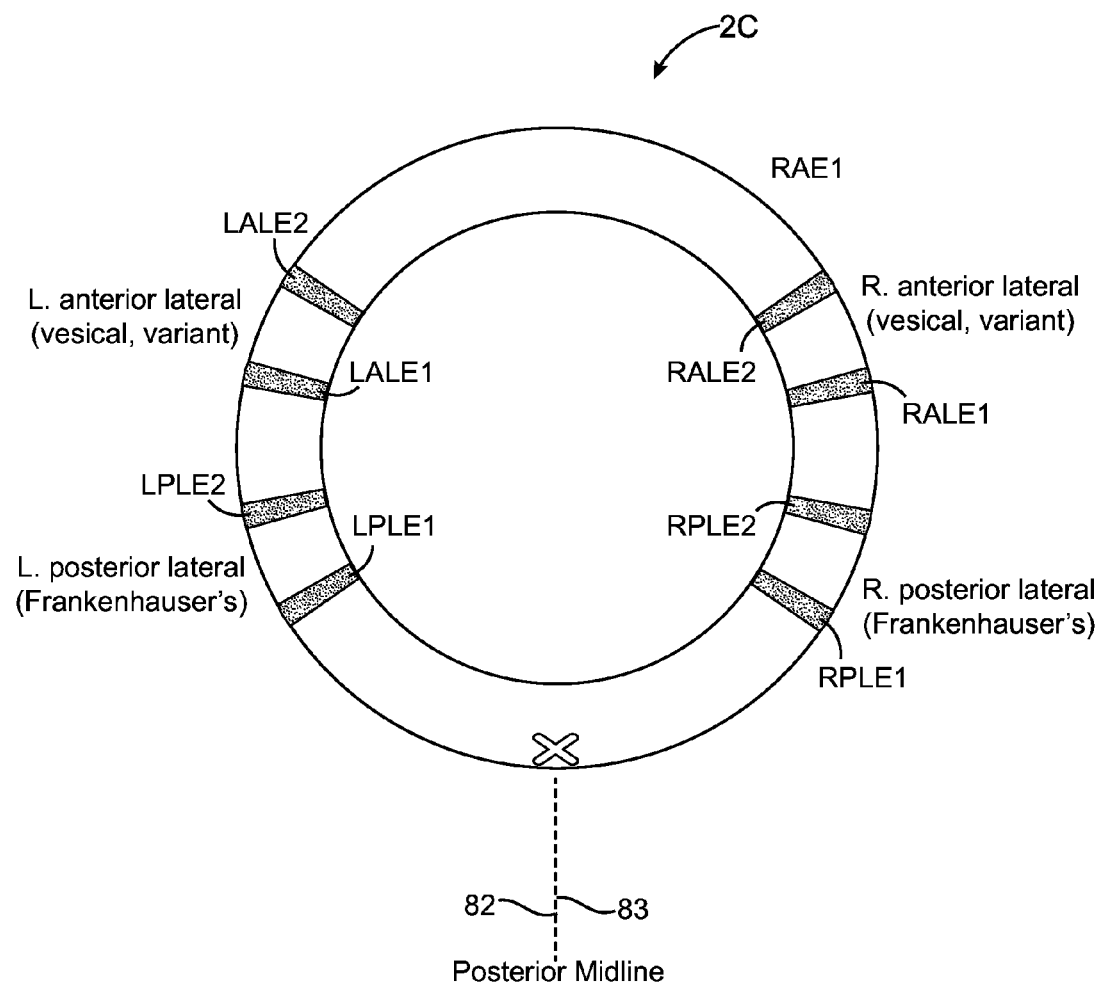
FIG. 22 shows another device for stimulating nerves.
Figure 23:
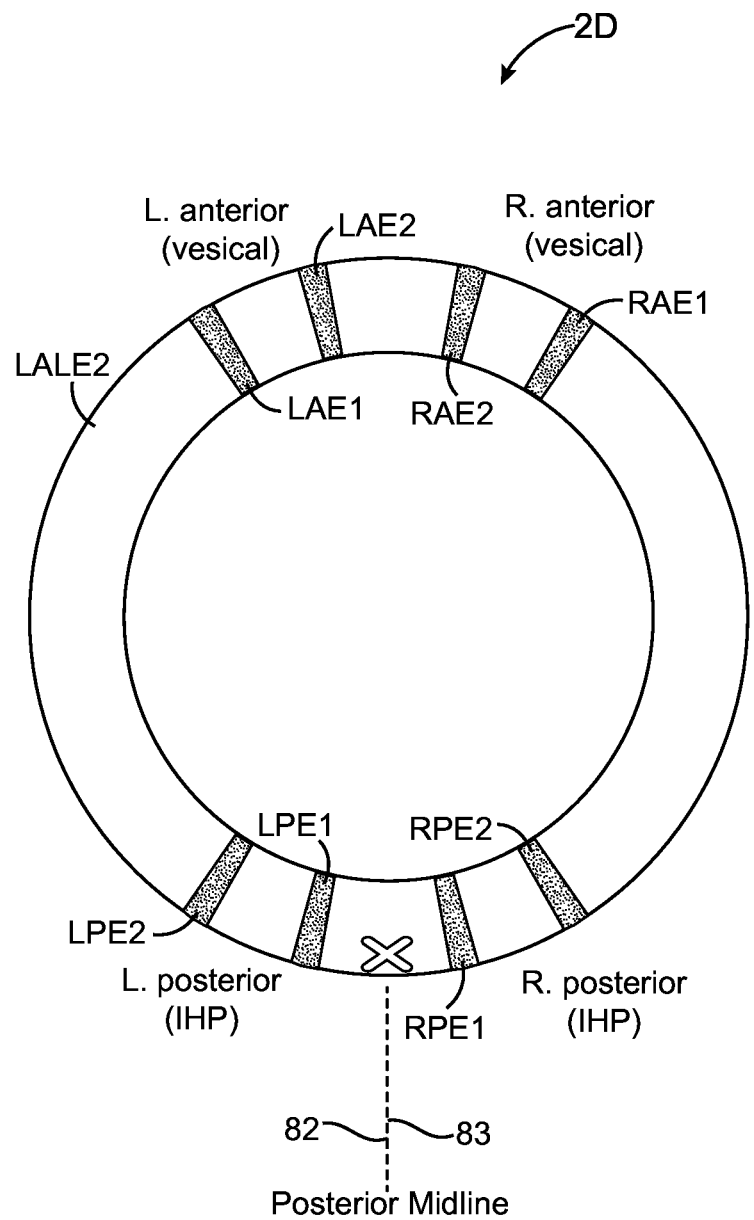
FIG. 23 shows another device for stimulating nerves for use with the device of FIG. 22.
Figure 24:
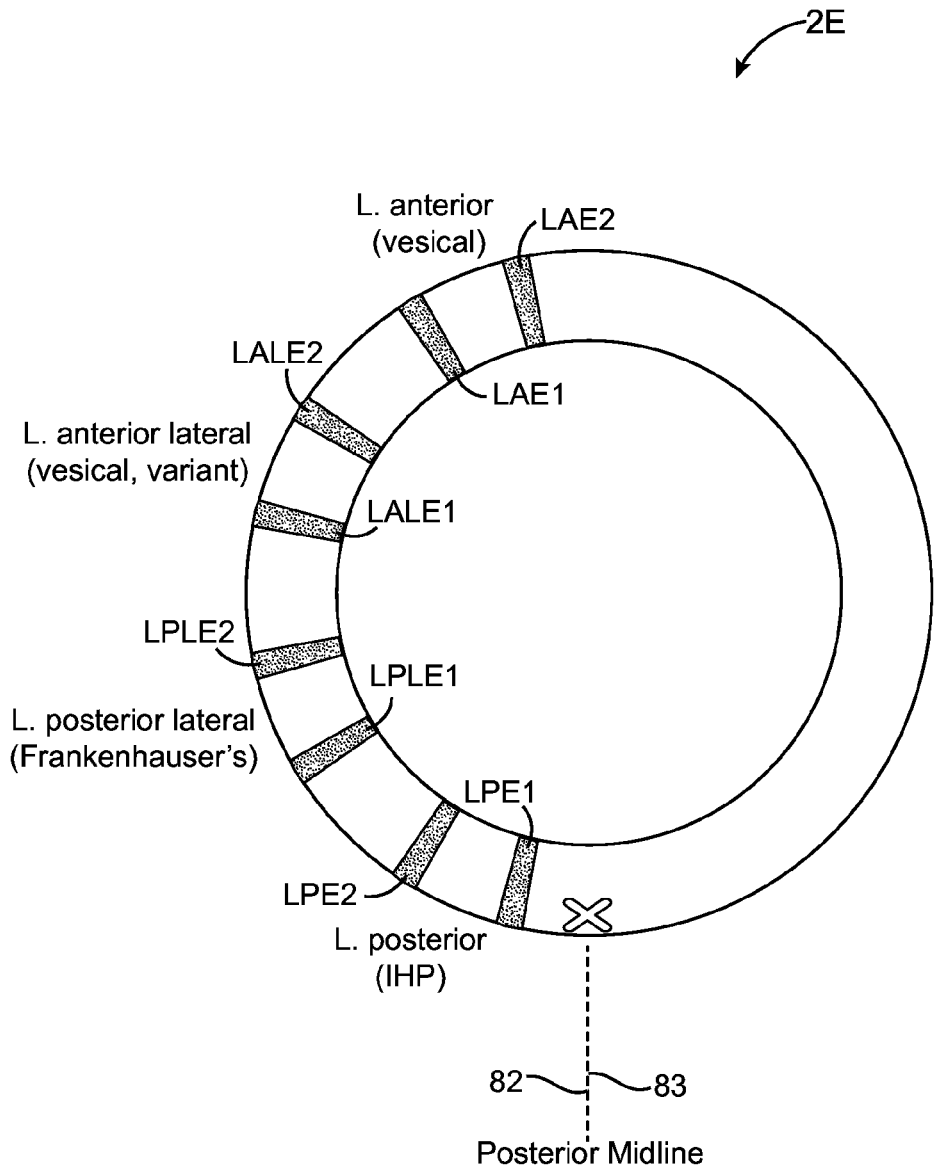
FIG. 24 shows another device for stimulating nerves.

In one aspect, a plurality of devices 2C, 2D, 2E, such as at least three, having different patterns of stimulating elements 6 may be provided as shown in FIGS. 22-24. Of course, any other suitable division of plexuses among the plurality of devices 2C, 2D, 2E may be provided. The user may switch between the devices 2C, 2D, 2E (or others with different patterns of elements) as desired. All aspects and methods of using the devices 2, 2A, 2B are incorporated here for use with the plurality of devices 2C, 2D, 2E as applicable.

Figure 25:
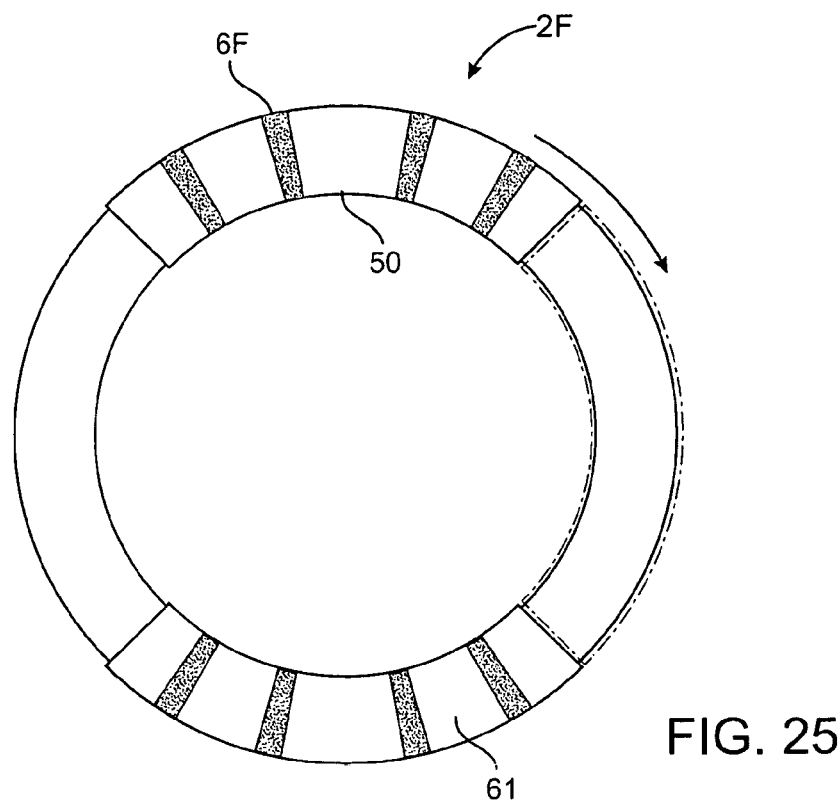
FIG. 25 shows another device for stimulating nerves with the nerve stimulating element mounted to a movable element on the body of the device.
Figure 26:
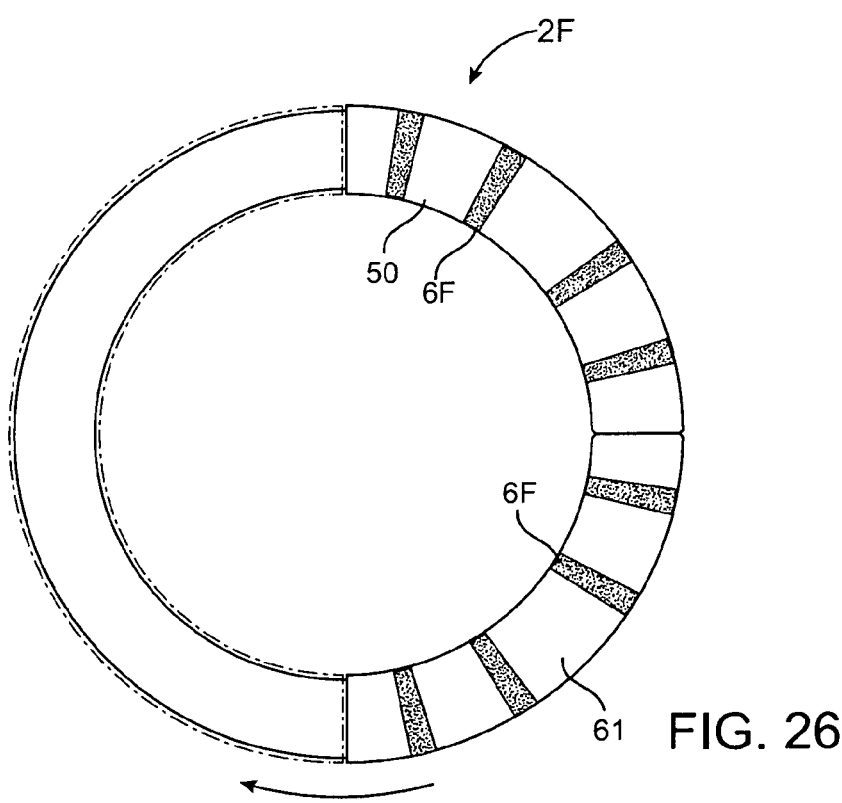
FIG. 26 shows the movable elements of FIG. 25 moved together.

Referring to FIGS. 25 and 26, the ability to select areas for stimulation may also be provided using device 2F having first and second movable elements 50, 61. The first and second movable elements 50, 52 are coupled to a support body 4F which may extend in an arc of at least 270 degrees for positioning around the cervix. Each of the movable elements 50, 52 includes elements 6F for stimulating nerves and all aspects described herein of the devices 2, 2A, 2B, and 2C-2E are incorporated here. The first and second movable elements 50, 52 permit the user to move the elements 6F to desired positions for stimulating target plexuses. FIG. 25 shows the movable elements 50, 52 positioned to stimulate nerves when positioned on opposing sides of the cervix (any opposing regions). FIG. 26 shows the movable elements 50, 52 moved together to form a section which permits stimulating half of the regions discussed herein and such uses are expressly incorporated here.

Figure 27:
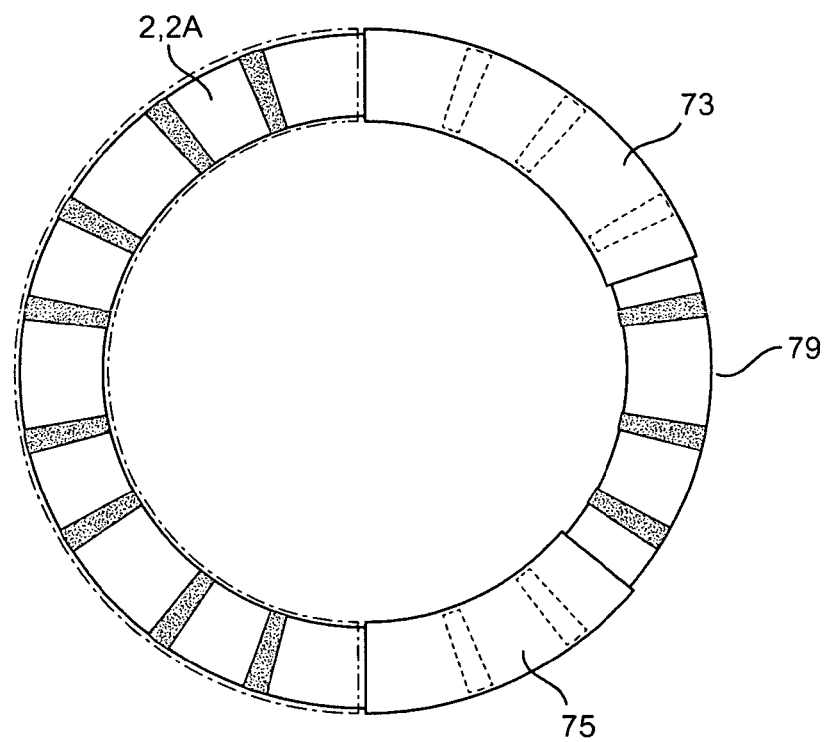
FIG. 27 shows a first cover and a second cover for covering parts of the devices described herein.

Referring to FIG. 27, a first cover 73 and a second cover 75 are provided to prevent or reduce stimulating some areas for use with any of the devices 2, 2A-2F described herein. The first and second covers 73, 75 are movable along the body to cover elements 6 as desired. The first and second covers may 73, 75 may also be spaced apart to form a window 79 for stimulating tissue within the window 79.

In still another aspect of the present invention, the device 2 is now referred to again with reference to FIGS. 1-22. The device 2 itself may be used to orient the device 2 within the patient using the nerve stimulating elements 6 themselves. For example, when one of the nerve stimulating elements 6 emits energy, another of the nerve stimulating elements 6 may measure energy received from the emitting element 6. The control system 18 monitors the energy received at the other nerve stimulating element 6 and records data regarding the energy received. The control system 18 may then recognize the orientation of the device 2 relative to the cervix by recognizing a pattern in the energy received. In another aspect, the control system 18 may simply measure impedance between two or more nerve stimulating elements. The resulting impedance data may also be subsequently used to orient the device 2 with the control system 18 recognizing a pattern of data to orient the device 2. Stated another way, the control system 18 may be used to orient the device with at least one of the nerve stimulating elements emitting energy and at least one other of the nerve stimulating elements measuring the energy emitted. The control system 18 may save a pattern of a parameter and compare the pattern to current data to orient the device about the cervix. For example, RF energy or ultrasound energy may be emitted by one or more elements 6 and received at others with the control system 18 monitoring and storing the data. In another aspect, impedance between nerve stimulating elements 6 may be used with the control system 18 monitoring and storing the impedance and matching a pattern of saved impedance data to orient the device 2, 2A. The device 2 may then change the pattern of stimulation using the nerve stimulating elements 6 in accordance with the orientation determined by the control system 18. Of course, an angular shift of the device 2 around the cervix may orient different elements 6 adjacent different targets but, of course, such a shift and change of nerve stimulating elements 6 is clearly contemplated with the present invention and, as such, the particular elements 6 used to stimulate the target area (plexus) may change.

The present invention may be used to treat a number of different conditions such as urge, frequency, nocturia, urge incontinence, stress incontinence, loss of urine without sensory awareness, bladder pain, urethral pain, urethral syndrome, urinary hesitancy, pelvic floor dyssynergia, interstitial cystitis, dysuria, overactive bladder, urinary retention, hesitancy, protracted urinary stream, dysmenorrhea, pelvic pain, pelvic venous congestion syndrome, endometriosis, irritable bowel syndrome, constipation, fecal urgency, fecal incontinence, rectal pain, pain with defecation, and anal pain. Of course, other uses of the present invention may become apparent without departing from the scope of the invention.

The present invention has been described in connection with preferred embodiments but it is understood that numerous modifications could be made to the preferred embodiments without departing from the scope of the invention. For example, the body could be V-shaped or the nerve stimulating element could be a coil through which a current is passed to induce and emit a magnetic field without departing from numerous aspects of the present invention.

What is claimed is:

1. A method of stimulating nerves adjacent a vaginal canal, comprising the steps of:
    positioning a device in the vagina, the device including a body and a first nerve stimulating element coupled to the body;
    stimulating nerves adjacent the vaginal canal using the first nerve stimulating element;
    the positioning step being carried out with the body extending at least 270 degrees around the cervix.

2. The method of claim 1, wherein:
    the positioning step is carried out with the body having a central opening, the cervix being positioned in the central opening.

3. A method of stimulating nerves adjacent a vaginal canal, comprising the steps of:
    positioning a device in the vagina, the device including a body and a first nerve stimulating element coupled to the body;
    stimulating nerves adjacent the vaginal canal using the first nerve stimulating element;
    the positioning step being carried out with the body extending completely around the cervix.

4. The method of claim 3, wherein:
    the positioning step is carried out with the body having a central opening, the cervix being positioned in the central opening.

5. A method of stimulating nerves adjacent a vaginal canal, comprising the steps of:
    positioning a device in the vagina, the device including a body and a first nerve stimulating element coupled to the body;
    stimulating nerves adjacent the vaginal canal using the first nerve stimulating element;
    orienting the device about the cervix using the first nerve stimulating element, the orienting step is carried out with the device having a control system, the control system saving a pattern in a parameter, the control system comparing the pattern in the parameter to current data to orient the device about the cervix.

6. The method of claim 5, wherein:
    the orienting step is carried out with the pattern being an impedance pattern.

* * * * *